(12) United States Patent
Nagashima et al.

(10) Patent No.: US 10,330,534 B2
(45) Date of Patent: Jun. 25, 2019

(54) COLORIMETRIC DEVICE AND PRINTING APPARATUS

(71) Applicant: KONICA MINOLTA, INC., Chiyoda-ku (JP)

(72) Inventors: Yoshiyuki Nagashima, Sakai (JP); Yuzuru Yamamoto, Osakasayama (JP)

(73) Assignee: KONICA MINOLTA, INC., Tokyo (JP)

(*) Notice: Subject to any disclaimer, the term of this patent is extended or adjusted under 35 U.S.C. 154(b) by 31 days.

(21) Appl. No.: 15/535,871

(22) PCT Filed: Nov. 24, 2015

(86) PCT No.: PCT/JP2015/082836
§ 371 (c)(1),
(2) Date: Jun. 14, 2017

(87) PCT Pub. No.: WO2016/098528
PCT Pub. Date: Jun. 23, 2016

(65) Prior Publication Data
US 2018/0364102 A1 Dec. 20, 2018

(30) Foreign Application Priority Data
Dec. 16, 2014 (JP) .................................. 2014-253937

(51) Int. Cl.
*G01J 3/52* (2006.01)
*G01J 3/02* (2006.01)
(Continued)

(52) U.S. Cl.
CPC ............. *G01J 3/524* (2013.01); *G01J 3/0202* (2013.01); *G01J 3/46* (2013.01); *G01J 3/465* (2013.01);
(Continued)

(58) Field of Classification Search
CPC .......... G01J 3/524; G01J 3/0202; G01J 3/465; H04N 1/40; H04N 1/46; H04N 1/56;
(Continued)

(56) References Cited

U.S. PATENT DOCUMENTS 5,369,494 A 11/1994 Bowden et al.
7,650,093 B2 1/2010 Suzuki
(Continued)

FOREIGN PATENT DOCUMENTS

JP 8-511618 12/1996
JP 2005-311644 11/2005
(Continued)

*Primary Examiner* — Jamil Ahmed
(74) *Attorney, Agent, or Firm* — Cozen O'Connor

(57) ABSTRACT

A backing member (50a) is pressed in a perpendicular direction (D3) by a predetermined sheet conveyed to a colorimetric position (P), and is disposed behind the predetermined sheet at the colorimetric position (P) when viewed from a colorimetric unit (40). A supporter (90) supports the backing member (50a) in a manner that the backing member (50a) can move in the perpendicular direction (D3). Holders (23a, 23b, 23c) hold a color tile member (80a) disposed on the backing member (50a) in a state that the amount of movement of the backing member (50a) in the perpendicular direction (D3) by the color tile member (80a) being thicker than the predetermined sheet and disposed on the backing member (50a) is larger than the amount of movement of the backing member (50a) in the perpendicular direction (D3) by the predetermined sheet.

17 Claims, 16 Drawing Sheets

(51) Int. Cl.
    *G01J 3/46*     (2006.01)
    *H04N 1/00*     (2006.01)
    *G01N 21/86*     (2006.01)

(52) U.S. Cl.
    CPC ..... *H04N 1/00087* (2013.01); *H04N 1/00602* (2013.01); *G01J 3/02* (2013.01); *G01J 3/52* (2013.01); *G01N 2021/8654* (2013.01)

(58) Field of Classification Search
    CPC .. H04N 1/60; H04N 1/00015; H04N 1/00087; H04N 1/00602; G01N 2021/8654; G03G 15/00; G03G 15/02; G03G 15/04; G03G 15/16; G03G 15/5062
    See application file for complete search history.

(56) References Cited

U.S. PATENT DOCUMENTS

| | | | |
|---|---|---|---|
| 8,755,701 B2 | 6/2014 | Hyoki | |
| 2005/0237548 A1* | 10/2005 | Suzuki | H04N 1/00015 358/1.9 |
| 2012/0070200 A1* | 3/2012 | Hyoki | G03G 15/5062 399/297 |

FOREIGN PATENT DOCUMENTS

| | | |
|---|---|---|
| JP | 2012-70023 | 4/2012 |
| JP | 2013-111758 | 6/2013 |
| JP | 2014-82680 | 5/2014 |

\* cited by examiner

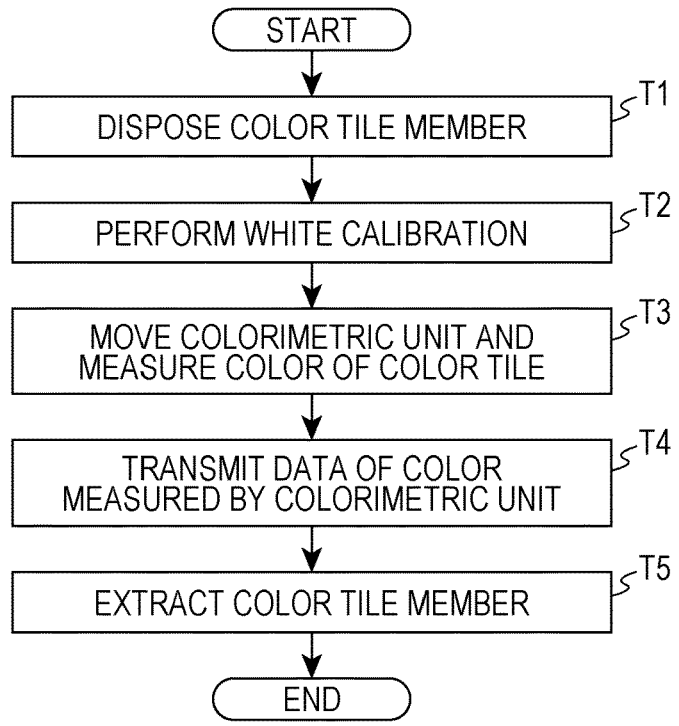
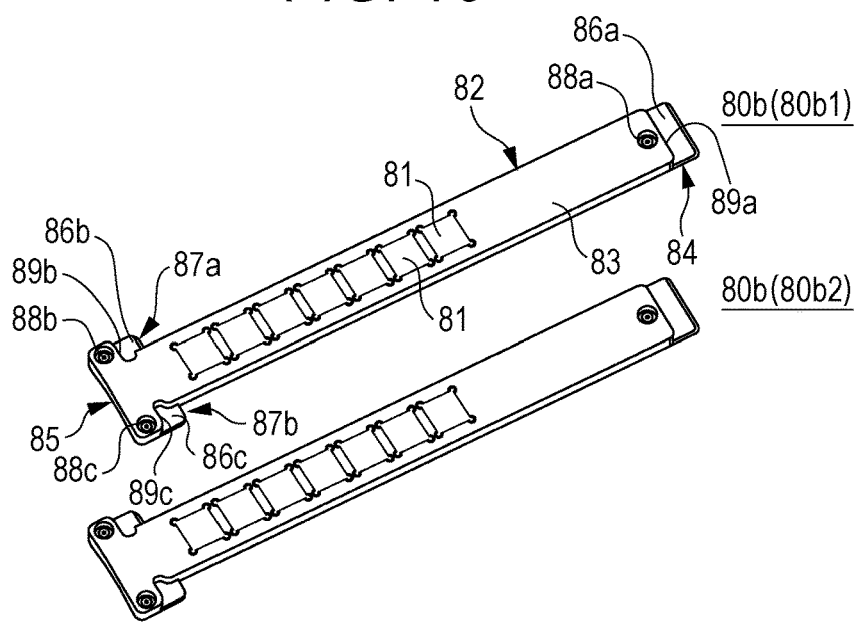

COLORIMETRIC DEVICE AND PRINTING APPARATUS

RELATED APPLICATIONS

This is a U.S. National Phase Application under 35 USC 371 of International Application PCT/JP2015/082836 filed on Nov. 24, 2015.

This application claims the priority of Japanese application no. 2014-253937 filed Dec. 16, 2014, the entire content of which is hereby incorporated by reference.

TECHNICAL FIELD

The present invention relates to a colorimetric device for measuring the color by conveying a predetermined sheet such as a color chart to a colorimetric position, and a printing apparatus including the colorimetric device.

BACKGROUND ART

In order to examine the color reproducibility of the color printing of a printing apparatus, a color chart printed by that printing apparatus is used. A color chart refers to a sheet of paper on which a plurality of color patches with the different hues, brightness, and chroma is printed. A user of the printing apparatus measures each color of the plurality of color patches included in the color chart by using a colorimetric device. The user then evaluates the amount of color shift between the color measured value and the color target value in regard to each of the plurality of color patches and examines the color reproducibility, and if he has determined that the color reproducibility is insufficient, he adjusts the printing apparatus.

One example of such a colorimetric device is disclosed in Patent Literature 1. In this colorimetric device, while a sheet on which a plurality of color patches is printed is conveyed in one direction, each color of the plurality of color patches is measured.

The accuracy of the colorimetric device is checked regularly and if the accuracy has decreased, the calibration is carried out. By measuring each color of a plurality of color tiles with different colors (for example, color tiles with 12 to 14 colors) with the use of the colorimetric device, the accuracy of the colorimetric device is checked. Since the color tile does not largely change in color over time, the color tile is used as the criterion of the color. In order to check the accuracy of the colorimetric device, a color tile member including a plurality of color tiles is prepared.

A color tile is much thicker than a color chart. Therefore, in the case of the colorimetric device that conveys the color chart to the colorimetric position and measures each color of the plurality of color patches at the colorimetric position, it is impossible that the color tile member is conveyed to the colorimetric position and successively the color tile member is disposed at that position.

In the colorimetric device, a white calibration plate is disposed at a position different from the colorimetric position. Similarly, in another embodiment, a color tile member is disposed at a position different from the colorimetric position. However, since the color tile member is formed of a plurality of color tiles, the area of the color tile member is relatively large. Thus, if a place exclusively used to install the color tile member is provided in the colorimetric device, such a colorimetric device becomes larger in size.

CITATION LIST

Patent Literature

Patent Literature 1: JP 8-511618 A

SUMMARY OF INVENTION

It is an object of the present invention to provide a colorimetric device that can achieve both the automatic measurement of a color chart and the measurement of a color tile member while preventing the size increase of the colorimetric device, and a printing apparatus including the colorimetric device.

A colorimetric device according to a first aspect of the present invention for achieving the above object includes: a colorimetric unit that measures a color of a subject positioned at a predetermined colorimetric position; a conveyance unit that conveys a predetermined sheet to the colorimetric position; a backing member that is pressed by the predetermined sheet conveyed to the colorimetric position by the conveyance unit in a perpendicular direction relative to a surface of the predetermined sheet, and is disposed behind the predetermined sheet at the colorimetric position when viewed from the colorimetric unit; a supporter that supports the backing member in a manner that the backing member can move in the perpendicular direction; and a holder that holds the color tile member disposed on the backing member in a state that the amount of movement of the backing member in the perpendicular direction by a color tile member being thicker than the predetermined sheet and disposed on the backing member is larger than the amount of movement of the backing member in the perpendicular direction by the predetermined sheet.

A colorimetric device according to a second aspect of the present invention for achieving the above object includes: a colorimetric unit that measures a color of a subject positioned at a predetermined colorimetric position; a conveyance unit that conveys a predetermined sheet to the colorimetric position; a backing member that includes a base member with a first surface and a second surface, and a background part provided for the first surface and that is disposed behind the predetermined sheet conveyed by the conveyance unit to the colorimetric position, when viewed from the colorimetric unit; a color tile member provided for the second surface; and a switching unit that switches between a first posture that the background part faces the colorimetric unit and a second posture that the color tile member faces the colorimetric unit, by rotating the base member at the colorimetric position.

A colorimetric device according to a third aspect of the present invention for achieving the above object includes: a colorimetric unit that measures a color of a subject positioned at a predetermined colorimetric position; a conveyance unit that conveys a predetermined sheet to the colorimetric position; an attachment unit to which a backing member disposed behind the predetermined sheet conveyed to the colorimetric position by the conveyance unit when viewed from the colorimetric unit is detachably attached; and a color tile member that is detachably attached to the attachment unit instead of the backing member in a state that the backing member is detached.

The aforementioned and other aspects, object, features, and advantageous effects of the present invention will be made apparent from the detailed description below and the attached drawings.

BRIEF DESCRIPTION OF DRAWINGS

FIG. 9 is a flowchart for describing the operation of measuring the colors of a plurality of color tiles using the colorimetric device according to the first embodiment.

FIG. 10 is a perspective view of two color tile members that can be attached to a colorimetric device according to a second embodiment.

DESCRIPTION OF EMBODIMENTS

Embodiments of the present invention will hereinafter be described in detail with reference to the drawings. In each drawing, the structures denoted by the same reference sign are the same, and the description already made on that structure is not repeated.

Figure 1:
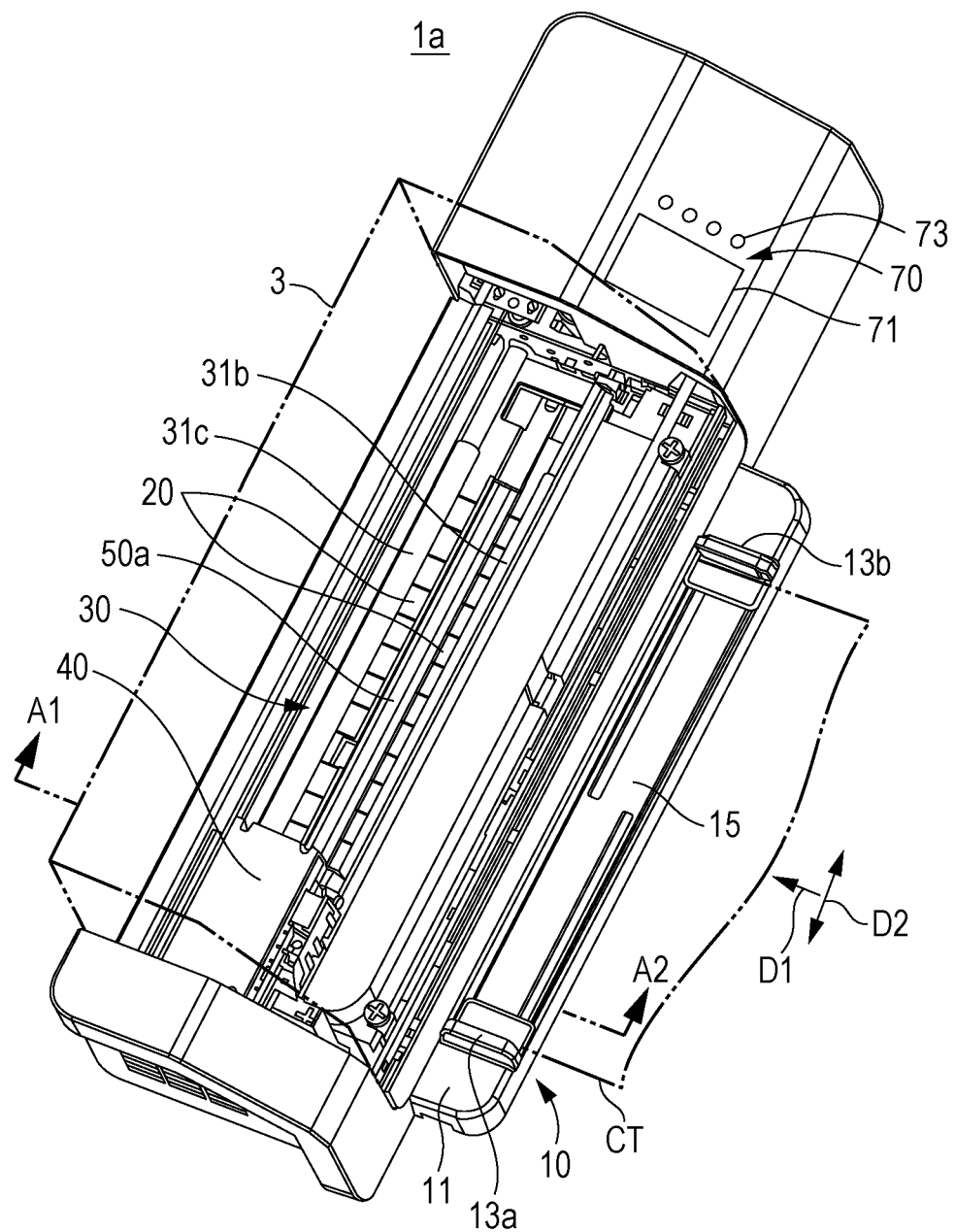
FIG. 1 is a perspective view of an external appearance of a colorimetric device according to a first embodiment of the present invention.
Figure 2:
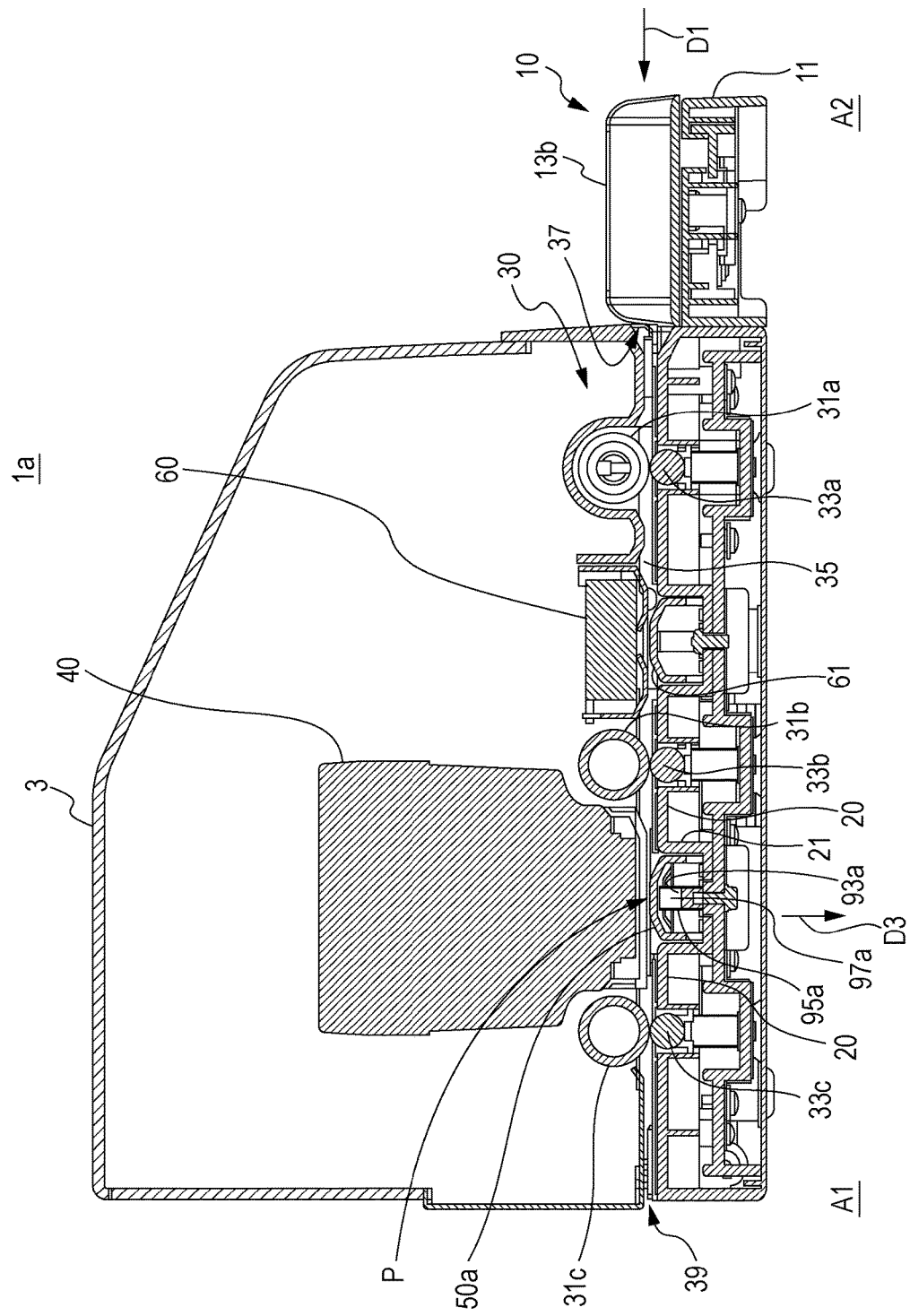
FIG. 2 is a cross-sectional view of the colorimetric device illustrated in FIG. 1, which is taken along a line A1-A2.

FIG. 1 is a perspective view of an external appearance of a colorimetric device 1a according to a first embodiment of the present invention. FIG. 2 is a cross-sectional view of the colorimetric device 1a illustrated in FIG. 1, which is taken along a line A1-A2. FIG. 1 illustrates the colorimetric device 1a from which an exterior cover 3 has been detached, and FIG. 2 illustrates the colorimetric device 1a to which the exterior cover 3 has been attached.

Figure 3:
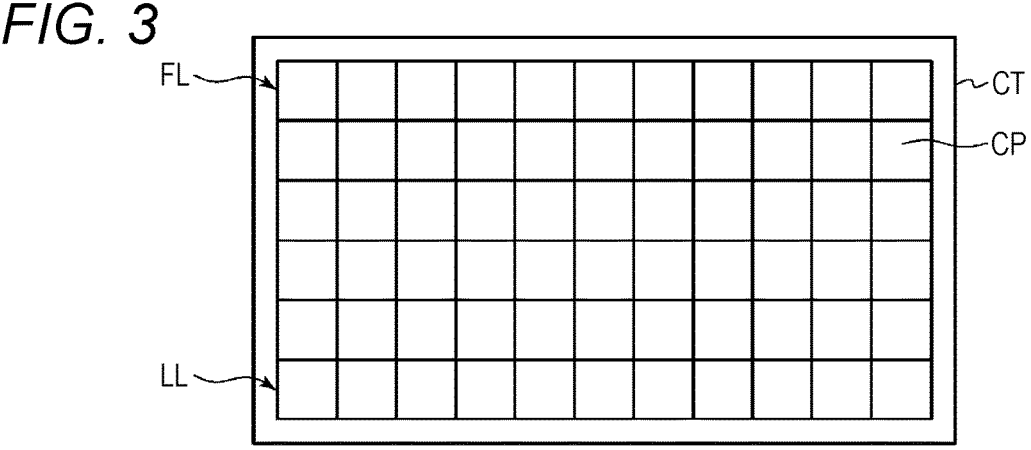
FIG. 3 is a plan view illustrating one example of a color chart.

The colorimetric device 1a includes a sheet feeding unit 10, a conveyance unit 30, a colorimetric unit 40, a backing member 50a, an imaging unit 60, an operation unit 70, and the exterior cover 3. As an example of a predetermined sheet to be subjected to the colorimetry, a color chart CT is described. FIG. 3 is a plan view illustrating one example of the color chart CT. The color chart CT is a sheet of paper on which a plurality of color patches CP with various hues, brightness, and chroma is printed. A plurality of color patches CP with a rectangular shape is arranged in the two-dimensional array.

With reference to FIG. 1 and FIG. 2, the direction where the color chart CT is conveyed is a conveyance direction D1 and a direction where the colorimetric unit 40 moves is a movement direction D2. The conveyance direction D1 and the movement direction D2 are orthogonal to each other. The movement direction D2 coincides with a main scanning direction and the conveyance direction D1 coincides with a sub-scanning direction.

The sheet feeding unit 10 includes a sheet feeding main body unit 11 and a pair of sheet feeding guides 13a and 13b. The sheet feeding main body unit 11 includes a sheet receiving surface 15 that receives the incoming color chart CT. The pair of sheet feeding guides 13a and 13b is attached to the sheet feeding main body unit 11 in a manner that the sheet feeding guides 13a and 13b can move on the sheet receiving surface 15 along the movement direction D2. With the pair of sheet feeding guides 13a and 13b, the color chart CT is guided toward the conveyance unit 30.

The conveyance unit 30 includes a conveyance path 35, a first driving roller 31a, a second driving roller 31b, a third driving roller 31c, a first driven roller 33a, a second driven roller 33b, and a third driven roller 33c.

The conveyance path 35 is a path where the color chart CT moves in the conveyance unit 30, and is connected to an inlet 37 and an outlet 39 of the conveyance unit 30. The inlet 37 is connected to the sheet feeding unit 10, and the color chart CT set in the sheet feeding unit 10 enters the conveyance unit 30 through the inlet 37, goes through the conveyance path 35 and then exits from the colorimetric device 1a through the outlet 39.

The first driving roller 31a, the second driving roller 31b, and the third driving roller 31c are disposed on the conveyance path 35 with a space therebetween. The first driving roller 31a is disposed near the inlet 37, the third driving roller 31c is disposed near the outlet 39, and the second driving roller 31b is disposed between the first driving roller 31a and the third driving roller 31c.

The first driven roller 33a is disposed to face the first driving roller 31a, the second driven roller 33b is disposed to face the second driving roller 31b, and the third driven roller 33c is disposed to face the third driving roller 31c.

The color chart CT moves in the conveyance path 35 along the conveyance direction D1 while being held between the first driving roller 31a and the first driven roller 33a that are rotated, between the second driving roller 31b and the second driven roller 33b that are rotated, and between the third driving roller 31c and the third driven roller 33c that are rotated.

The colorimetric unit 40 is disposed on the conveyance path 35 between the second driving roller 31b and the third driving roller 31c. The backing member 50a is disposed below the conveyance path 35 to face an optical system (not shown) in the colorimetric unit 40. In the conveyance path 35 between the colorimetric unit 40 and the backing member 50a, a colorimetric position P exists. The color chart CT is conveyed to the colorimetric position P by the conveyance unit 30.

The colorimetric unit 40 is a device that measures the color of a subject (measurement subject) present at the colorimetric position P. The colorimetric unit 40 is, for example, a colorimetric sensor that acquires predetermined optical information of the measurement subject in order to obtain the color of the measurement subject. Such a colorimetric unit 40 is a spectroscopic colorimeter including a spectroscopic element, a photoelectric conversion element, or the like to measure the reflectance (or transmittance) of each wavelength, and measures the color of the subject on the basis of the reflectance (or transmittance) of each wavelength. In another example, the colorimetric unit 40 is a tristimulus value colorimeter including an optical filter, a photoelectric conversion element, or the like to measure the tristimulus value of X, Y, and Z and measures the color of the subject on the basis of the color difference of the tristimulus value.

The colorimetric unit 40 is moved by a movement unit 6 (FIG. 4), which will be described below, in the movement direction D2 (in a direction orthogonal to the direction where the predetermined sheet is conveyed) in a state that the colorimetric unit 40 faces the backing member 50a.

The backing member 50a extends in the movement direction D2 and faces the trace where the colorimetric unit 40 moves. The backing member 50a is pressed by the color chart CT conveyed to the colorimetric position P in a perpendicular direction D3 relative to the surface of the color chart CT (i.e., in the direction of the thickness of the color chart CT). Thus, the backing member 50a is disposed behind the color chart CT when viewed from the colorimetric unit 40 at the colorimetric position P.

The backing member 50a is in contact with one surface of the color chart CT conveyed to the colorimetric position P (i.e., the surface opposite to the surface on which the plurality of color patches CP is printed).

The color of the backing member 50a is, for example, white or black. When the color of the color chart CT is measured by the colorimetric unit 40, the backing member 50a becomes the background (background color).

The imaging unit 60 is disposed on the conveyance path 35 between the first driving roller 31a and the second driving roller 31b.

The imaging unit 60 is a device that images the optical image of the subject. The imaging unit 60 includes, for example, a line sensor (a linear image sensor) having a plurality of photoelectric conversion elements arrayed in one direction, or the like, and the one direction is made to coincide with the main scanning direction (i.e., the movement direction D2) so that the imaging unit 60 is disposed extending in the main scanning direction.

A shading correction plate 61 is disposed below the conveyance path 35, facing the imaging unit 60. The shading correction plate 61 is a white plate and is used for shading correction of the imaging unit 60.

The exterior cover 3 covers the conveyance unit 30, the colorimetric unit 40, the backing member 50a, the imaging unit 60, and the shading correction plate 61.

The operation unit 70 includes a display unit 71 and operation buttons 73, and serves as the interface used to operate the colorimetric device 1a.

Figure 4:
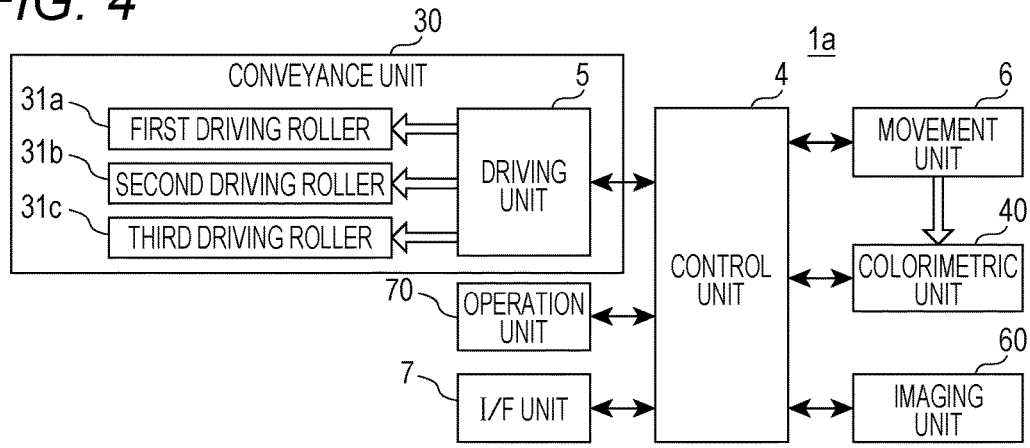
FIG. 4 is a block diagram illustrating an electric structure of the colorimetric device according to the first embodiment.

FIG. 4 is a block diagram illustrating an electric structure of the colorimetric device 1a. The colorimetric device 1a includes the colorimetric unit 40, the imaging unit 60, the operation unit 70, a control unit 4, a driving unit 5, the movement unit 6, and an I/F unit 7. The description on the colorimetric unit 40, the imaging unit 60, and the operation unit 70 is omitted because they are already described.

The control unit 4 includes a CPU, a memory, and the like, and collectively controls the colorimetric device 1a. The colorimetric unit 40 and the imaging unit 60 are controlled by the control unit 4.

The driving unit 5 is an element that forms the conveyance unit 30. The driving unit 5 includes, for example, a stepping motor and rotates the first driving roller 31a, the second driving roller 31b, and the third driving roller 31c in accordance with the control by the control unit 4. In the driving unit 5, the stepping motor is rotated by a predetermined angle when one driving pulse is input, and by this rotation of the stepping motor, the first driving roller 31a, the second driving roller 31b, and the third driving roller 31c are rotated by a predetermined angle. By the rotations of these driving rollers, the color chart CT is conveyed (moved) by a predetermined amount along the conveyance direction D1.

The movement unit 6 is a movement mechanism that moves the colorimetric unit 40 in the movement direction D2 (main scanning direction) for each predetermined amount by a predetermined unit conveyance order in accordance with the control by the control unit 4. The movement unit 6 includes, for example, a guide member that guides the colorimetric unit 40, a feeding mechanism that moves the colorimetric unit 40 by causing the guide member to guide the colorimetric unit 40, such as a rack pinion or a feeding screw, and a feeding mechanism driving unit that drives the feeding mechanism, such as a stepping motor.

The I/F unit 7 is an interface that is connected to an external device such as a personal computer. The measurement results from the colorimetric device 1a are sent to the personal computer through the I/F unit 7 and stored in the personal computer. The measurement results are displayed on a display portion of the personal computer.

Figure 5:
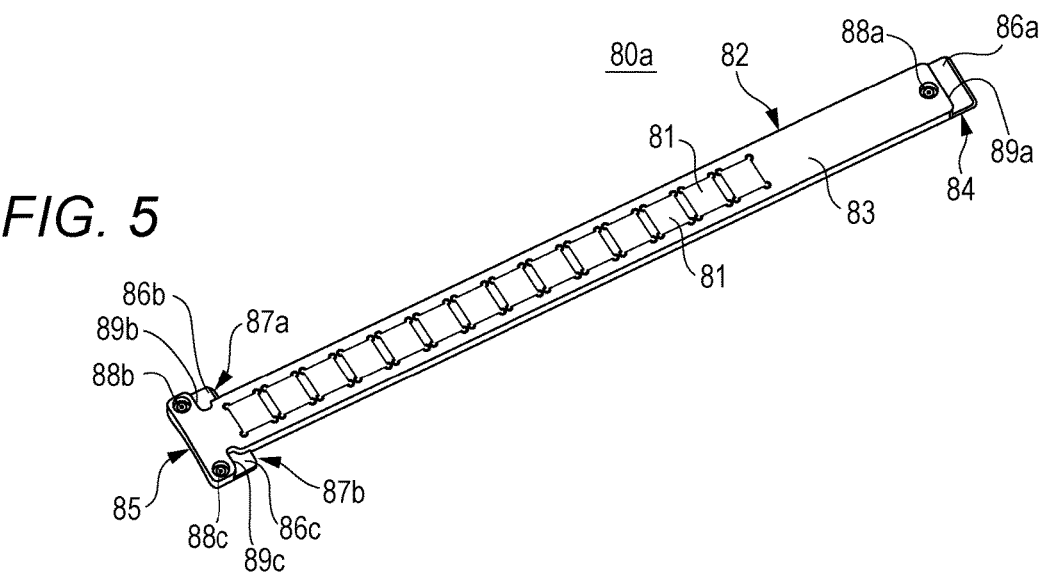
FIG. 5 is a perspective view of a color tile member that can be attached to the colorimetric device according to the first embodiment.

FIG. 5 is a perspective view of a color tile member 80a that can be attached to the colorimetric device 1a according to the first embodiment. The color tile member 80a includes a plurality of color tiles 81 and a substrate 82.

The plurality of color tiles 81 differs from each other in color. Although FIG. 5 illustrates 14 color tiles 81, the number of color tiles 81 is not limited to 14.

The substrate 82 includes a main body part 83, and one end part 84 and the other end part 85 at opposite ends of the main body part 83.

The main body part 83 has a long and narrow shape. The plurality of color tiles 81 is arranged in a longitudinal direction of the main body part 83, and is fixed to the main body part 83.

The one end part 84 is provided with a slide plane 86a with smaller height than the surface of the main body part 83. The border between the slide plane 86a and the main body part 83 corresponds to a step part 89a.

Of the substrate 82, the other end part 85 is wider than the main body part 83 in width. The other end part 85 has protrusions 87a and 87b protruding from the substrate 82 in a minor-axis direction of the substrate 82. The protrusion 87a has a step part 89b, and is provided with a slide plane 86b with smaller height than the surface of the main body part 83 with the step part 89b serving as the border. Similarly, the protrusion 87b has a step part 89c, and is provided with a slide plane 86c with smaller height than the surface of the main body part 83 with the step part 89c serving as the border.

The main body part 83 is provided with a ball plunger 88a near the one end part 84. In the protrusion 87a, a ball plunger 88b is provided next to the slide plane 86b. In the protrusion 87b, a ball plunger 88c is provided next to the slide plane 86c.

Figure 6:
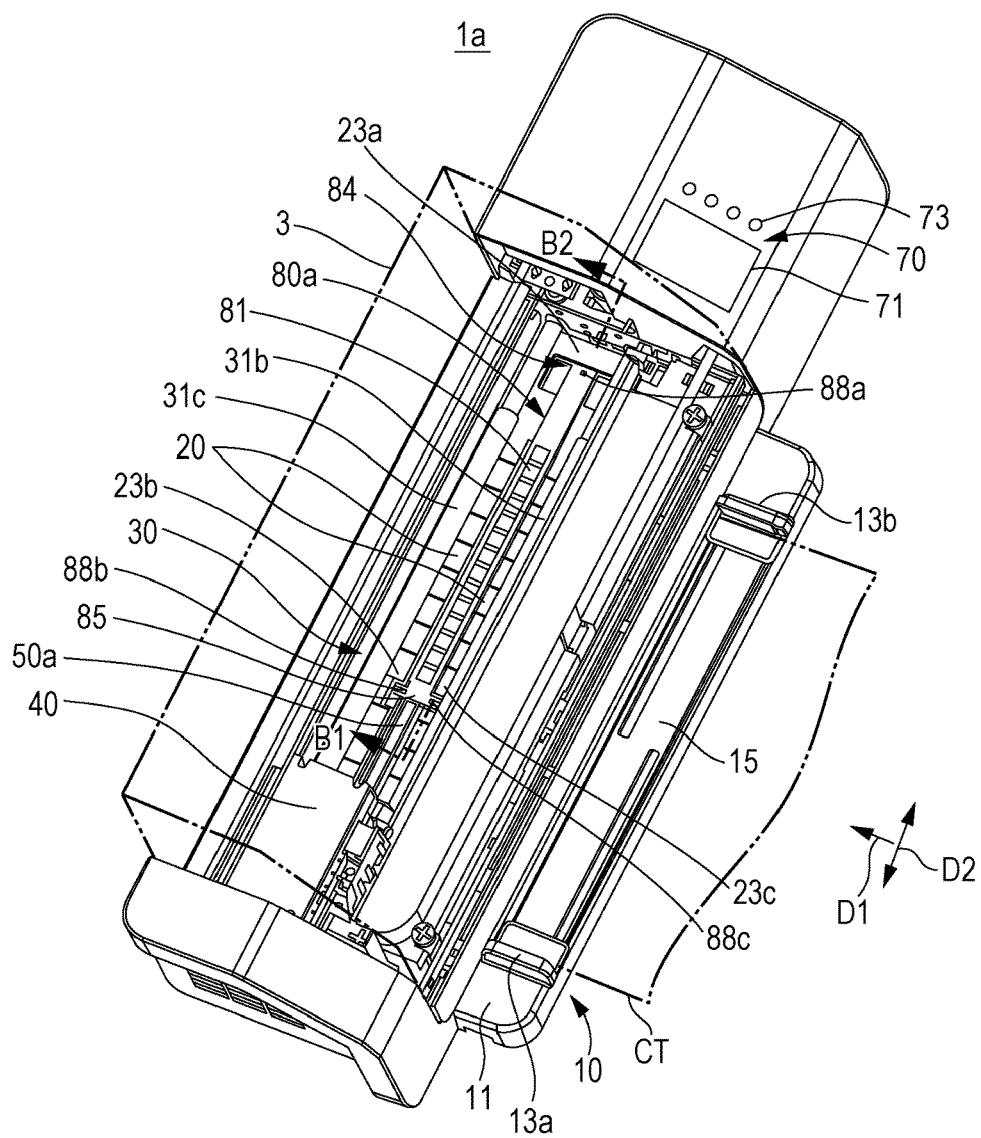
FIG. 6 is a perspective view of the external appearance of the colorimetric device according to the first embodiment to which the color tile member is attached.
Figure 7:
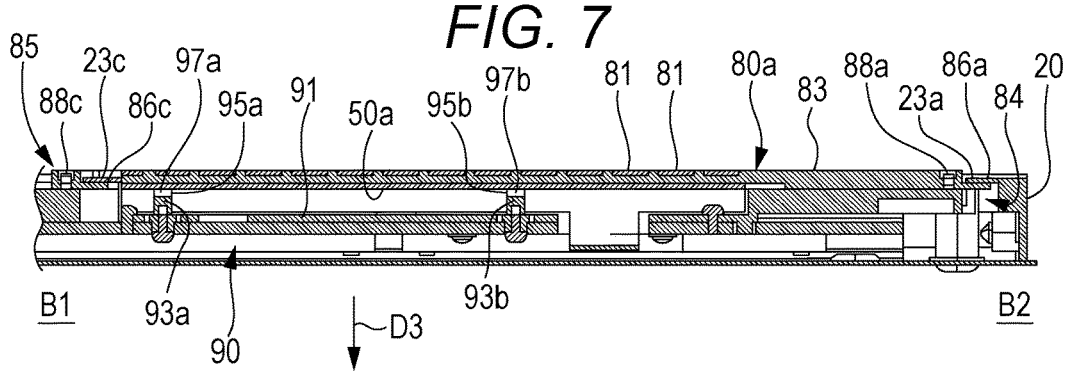
FIG. 7 is a cross-sectional view of the colorimetric device illustrated in FIG. 6, which is taken along a line B1-B2.

FIG. 6 is a perspective view illustrating an external appearance of the colorimetric device 1a according to the first embodiment to which the color tile member 80a is attached. FIG. 6 is different from FIG. 1 in that the color tile member 80a is fixed on the backing member 50a. FIG. 7 is a cross-sectional view of the colorimetric device 1a illustrated in FIG. 6, which is taken along a line B1-B2.

With reference to FIG. 2, FIG. 6, and FIG. 7, the conveyance unit 30 includes a base member 20 constituting a part of the conveyance path 35. The base member 20 is disposed between the second driven roller 33b and the third driven roller 33c, and includes a recessed part 21 (FIG. 2) extending in the movement direction D2. The recessed part 21 is disposed facing the trace where the colorimetric unit 40 moves.

The backing member 50a is fitted to the recessed part 21. The backing member 50a is pressed by the color chart CT conveyed to the colorimetric position P in the perpendicular direction D3 relative to the surface of the color chart CT (FIG. 2).

A supporter 90 (FIG. 7) supports the backing member 50a in a manner that the backing member 50a can move in the perpendicular direction D3. The supporter 90 includes a platform 91, bosses 93a and 93b, and springs 95a and 95b.

The bottom wall of the recessed part 21 serves as the platform 91. On the platform 91, the boss 93a and the boss 93b are attached with a space therebetween. The boss 93a has the spring 95a fitted thereto, and the boss 93b has the spring 95b fitted thereto. The springs 95a and 95b are the compression springs. Each of the springs 95a and 95b has its end fixed at a back surface of the backing member 50a. Between the end of the boss 93a and the end of the spring 95a, a space portion 97a is formed and this space portion 97a enables the backing member 50a to move in the perpendicular direction D3. Similarly, between the end of the boss 93b and the end of the spring 95b, a space portion 97b is formed and this space portion 97b enables the backing member 50a to move in the perpendicular direction D3.

The backing member 50a is supported at a predetermined height by the springs 95a and 95b when not pressed. When the backing member 50a is pressed in the perpendicular direction D3, the springs 95a and 95b are compressed to make the backing member 50a go down in the perpendicular direction D3. As the thickness of the color chart CT conveyed to the colorimetric position P is increased, the backing member 50a goes down further. When the pressing is cancelled, the backing member 50a rises back to the predetermined height in the perpendicular direction D3 by the biasing force of the springs 95a and 95b.

With reference to FIG. 5, FIG. 6, and FIG. 7, the color tile member 80a disposed on the backing member 50a is held by three holders 23a, 23b, and 23c. The holders 23a, 23b, and 23c constitute a part of the base member 20. The holder 23a is used for the slide plane 86a of the color tile member 80a, the holder 23b is used for the slide plane 86b, and the holder 23c is used for the slide plane 86c.

The slide plane 86a of the color tile member 80a is in contact with the holder 23a below the holder 23a. The slide plane 86b is in contact with the holder 23b below the holder 23b. The slide plane 86c is in contact with the holder 23c below the holder 23c. The color tile member 80a is held by the holders 23a, 23b, and 23c in a state of resisting the biasing force of the springs 95a and 95b.

The holders 23a, 23b, and 23c hold the color tile member 80a disposed on the backing member 50a in a state that the amount of movement of the backing member 50a in the perpendicular direction D3 by the color tile member 80a thicker than the color chart CT (corresponding to one example of predetermined paper) is larger than the amount of movement of the backing member 50a in the perpendicular direction D3 by the color chart CT.

The base member 20 has a groove (not shown) with a V-like cross-sectional shape, and each ball of the ball plungers 88a, 88b, and 88c is fitted to the groove. This prevents the color tile member 80a from sliding in the movement direction D2.

When a user holds the other end part 85 of the color tile member 80a with his fingers and pulls the other end part 85 in the movement direction D2 to the side opposite to the operation unit 70, each ball of the ball plungers 88a, 88b, and 88c is pulled out from the groove with the V-like sectional shape, and thus, the color tile member 80a can be extracted.

The color tile member 80a can be disposed on the backing member 50a by a method as below. When the user puts the color tile member 80a at a predetermined position on the backing member 50a and slides the color tile member 80a in the movement direction D2 toward the operation unit 70 in a state of pressing the color tile member 80a in the perpendicular direction D3, the slide plane 86a slides to the place under the holder 23a, the slide plane 86b slides to the place under the holder 23b, and the slide plane 86c slides to the place under the holder 23c. The color tile member 80a is slid until each ball of the ball plungers 88a, 88b, and 88c is fitted to the groove with the V-like cross-sectional shape.

Figure 8:
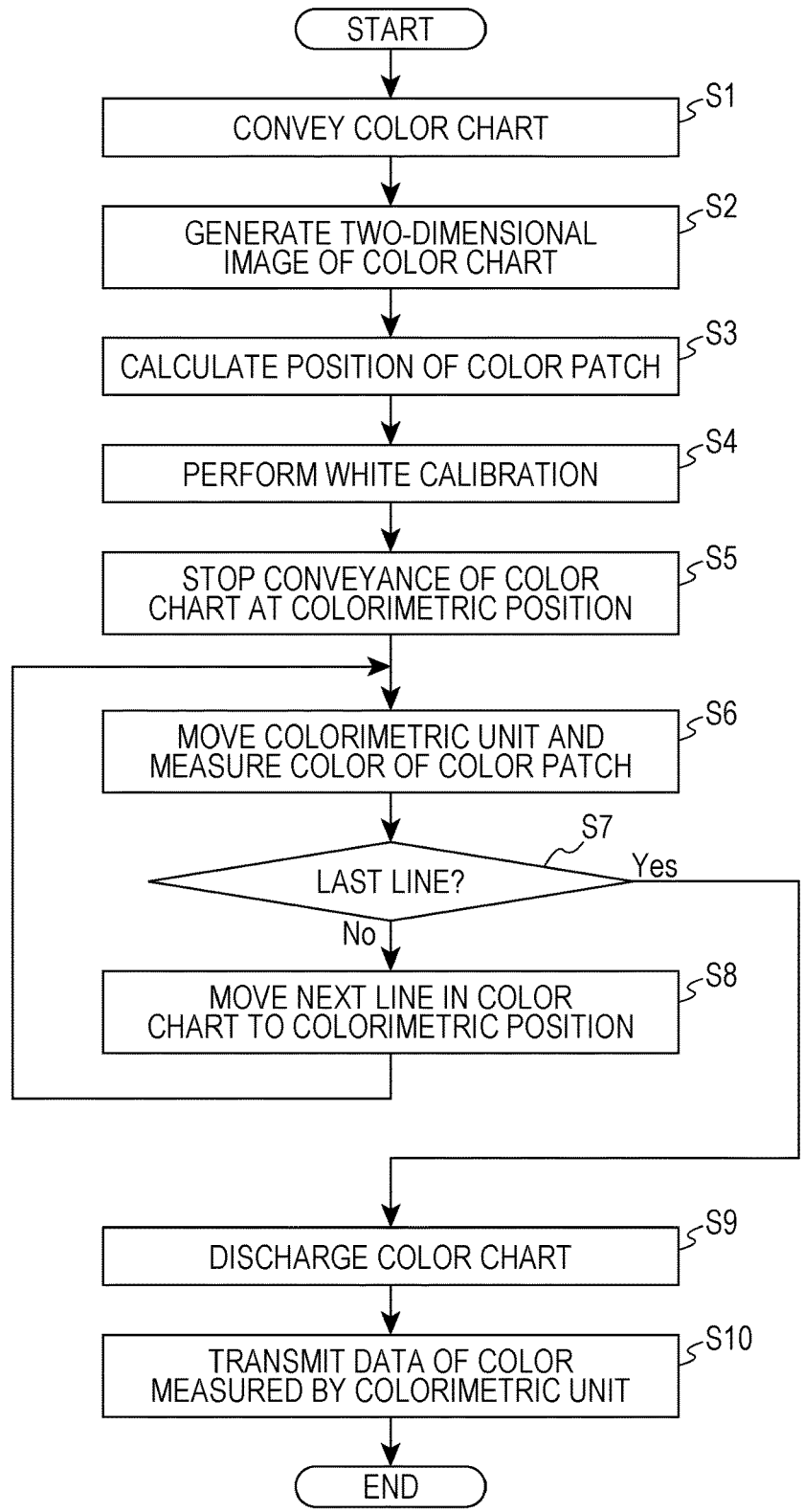
FIG. 8 is a flowchart for describing the operation of measuring the colors of a plurality of color patches using the colorimetric device according to the first embodiment.

The operation of measuring the color of the plurality of color patches CP illustrated in FIG. 3 using the colorimetric device 1a is described mainly with reference to FIG. 2 and FIG. 8. FIG. 8 is a flowchart for describing the operation. As described below, the colorimetric device 1a is configured to obtain a two-dimensional image of the color chart CT printed by a printing apparatus, which is the target of the colorimetry, calculate the position of each of the plurality of color patches CP by an image processing method using a computer, and measure the color of the color patch CP by moving the colorimetric unit 40 to the calculated position.

The user of the colorimetric device 1a sets to the sheet feeding unit 10 the color chart CT printed by the printing apparatus corresponding to the target of the colorimetry, manipulates the personal computer (not shown) connected to the colorimetric device 1a to set the color chart colorimetry mode, and inputs the start of the colorimetry. This causes the conveyance unit 30 to move the color chart CT set on the sheet feeding unit 10 on the conveyance path 35 along the conveyance direction D1 (step S1).

The imaging unit 60 scans the conveyed color chart CT and generates the data expressing the two-dimensional image of the color chart CT (step S2). The control unit 4 (FIG. 4) calculates the position of each of the plurality of color patches CP printed on the color chart CT using the two-dimensional image (step S3). The control unit 4 moves the colorimetric unit 40 to the calculated position and causes the colorimetric unit 40 to measure the color of each of the plurality of color patches CP as described below.

The colorimetric unit 40 performs the white calibration in order to start the colorimetry (step S4).

The conveyance unit 30 stops the conveyance of the color chart CT when the first line FL (FIG. 3) of the color chart CT has reached the colorimetric position P (step S5).

The movement unit 6 (FIG. 4) moves the colorimetric unit 40 to the place above the color patch CP in the order from the color patch CP closest to the colorimetric unit 40 in the color patch group constituting the first line FL. The colorimetric unit 40 repeats the operation of measuring the color of the color patch CP positioned below the colorimetric unit 40 (step S6). When the color of the last color patch CP in the color patch group has been measured, the control unit 4 (FIG. 4) determines whether the line formed by that color patch group is the last line LL (FIG. 3) or not (step S7).

When the control unit 4 has determined that the line formed by the color patch group is not the last line LL (No in step S7), the conveyance unit 30 moves the next line of the color chart CT to the colorimetric position P (step S8). The color patch group constituting the next line is subjected to the process of step S6.

When the control unit 4 has determined that the line formed by the color patch group is the last line LL (Yes in step S7), the conveyance unit 30 conveys the color chart CT and discharges the color chart CT out of the colorimetric device 1*a* through the outlet 39 (step S9).

The control unit 4 controls the I/F unit 7 (FIG. 4) and sends the data of the color measured by the colorimetric unit 40 to the personal computer connected to the colorimetric device 1*a* (step S10). The data are saved in the personal computer.

The operation of measuring the color of the plurality of color tiles 81 illustrated in FIG. 5 using the colorimetric device 1*a* is described mainly with reference to FIG. 2, FIG. 6, and FIG. 9. FIG. 9 is the flowchart for describing the operation.

The user opens the exterior cover 3, places the color tile member 80*a* on the backing member 50*a* (Step T1), and closes the exterior cover 3.

The user manipulates the personal computer (not shown) connected to the colorimetric device 1*a*, sets the color tile colorimetry mode, and inputs the start of the colorimetry.

The colorimetric unit 40 performs the white calibration in order to start the colorimetry (Step T2).

The movement unit 6 (FIG. 4) moves the colorimetric unit 40 to the place above the color tile 81 in order from the color tile 81 closest to the colorimetric unit 40, and the colorimetric unit 40 repeats the operation of measuring the color of the color tile 81 positioned below the colorimetric unit 40 (Step T3).

When the control unit 4 (FIG. 4) has determined that the colorimetric unit 40 finished measuring the color of the color tile 81, the control unit 4 controls the I/F unit 7 (FIG. 4) to send the data of the color measured by the colorimetric unit 40 to the personal computer connected to the colorimetric device 1*a* (Step T4). The data are saved in the personal computer.

The user extracts the color tile member 80*a* out of the colorimetric device 1*a* (Step T5).

The main effect of the first embodiment will be described. With reference to FIG. 7, the backing member 50*a* is movable in the perpendicular direction D3 relative to the color chart CT conveyed to the colorimetric position P (i.e., the direction of the thickness of the color chart CT). As the thickness of the color chart CT is increased, the amount of movement of the backing member 50*a* is increased; as the thickness of the color chart CT is decreased, the amount of movement of the backing member 50*a* is decreased.

The colorimetric device 1*a* according to the first embodiment includes the holders 23*a*, 23*b*, and 23*c* for holding the color tile member 80*a* disposed on the backing member 50*a*. The color tile member 80*a* is thicker than the color chart CT. The holders 23*a*, 23*b*, and 23*c* hold the color tile member 80*a* in a state that the amount of movement of the backing member 50*a* in the perpendicular direction D3 by the color tile member 80*a* disposed on the backing member 50*a* is larger than the amount of movement of the backing member 50*a* in the perpendicular direction D3 by the color chart CT conveyed to the colorimetric position P.

Therefore, even if the color tile member 80*a* is thicker than the color chart CT, the colorimetric device 1*a* according to the first embodiment can measure the color of the color tile member 80*a* disposed on the backing member 50*a*. Thus, both the automatic measurement of the color chart CT and the measurement of the color tile member 80*a* are possible while preventing the size increase of the colorimetric device 1*a*.

Figure 16:
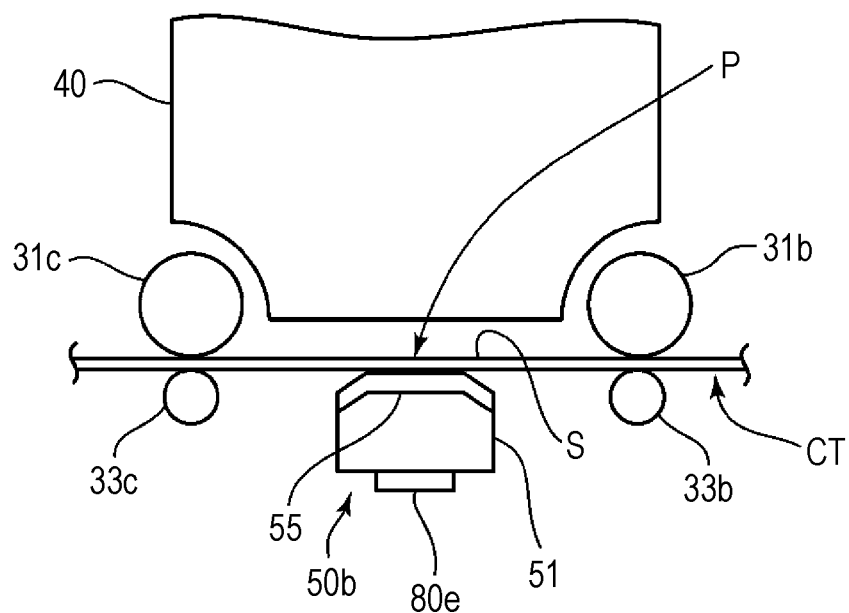
FIG. 16 is a schematic view illustrating a state in which the backing member included in the colorimetric device according to the fourth embodiment is in a first posture.
Figure 17:
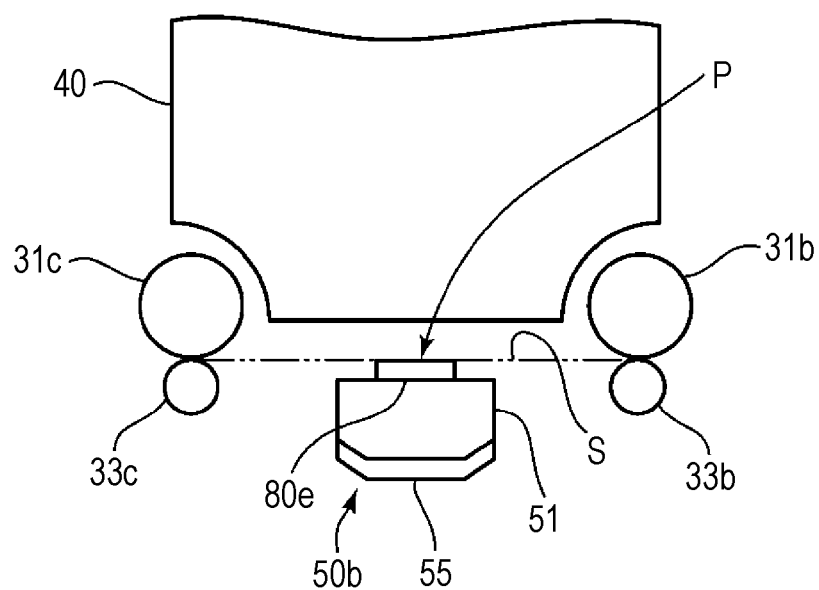
FIG. 17 is a schematic view illustrating a state in which the backing member included in the colorimetric device according to the fourth embodiment is in a second posture.

With reference to FIG. 2, the position on the surface of the color chart CT where the color patch CP (FIG. 3) is printed, which is opposite to the colorimetric unit 40, corresponds to the so-called sample surface S (measurement surface) illustrated in FIG. 16 and FIG. 17. The color chart CT is supported by being held between the second driving roller 31*b* and the second driven roller 33*b*, and between the third driving roller 31*c* and the third driven roller 33*c*. Therefore, the coordinate of the position on the roller surface of the second driving roller 31*b*, which is opposite to the roller surface of the second driven roller 33*b* (the position on the roller surface of the third driving roller 31*c*, which is opposite to the roller surface of the third driven roller 33*c*) coincides with that of the sample surface S (FIG. 16, FIG. 17) in the perpendicular direction D3. The holders 23*a*, 23*b*, and 23*c* (FIG. 6) hold the color tile member 80*a* so that the coordinate of the surface of the color tile 81 disposed on the color tile member 80*a* coincides with the coordinate of the sample surface S in the perpendicular direction D3.

That is to say, the conveyance unit 30 supports the color chart CT while the coordinate of the color chart CT in the perpendicular direction D3 at the colorimetric position P is set to a predetermined value. The holders 23*a*, 23*b*, and 23*c* hold the color tile member 80*a* while the coordinate of the surface of the color tile 81 of the color tile member 80*a* in the perpendicular direction D3 is set to the predetermined value.

Thus, according to the first embodiment, the coordinate of the color chart CT and the coordinate of the surface of the color tile 81 of the color tile member 80*a* are the same in the perpendicular direction D3 at the colorimetric position P. Accordingly, the distance from the optical system (not shown) of the colorimetric unit 40 to the color chart CT and the distance from the optical system of the colorimetric unit 40 to the surface of the color tile 81 become the same. As a result, as compared to the case in which they are different, the accuracy of examining the colorimetric device 1a can be increased.

A second embodiment will be described. As illustrated in FIG. 5, the color tile member 80a according to the first embodiment has a structure in which the plurality of color tiles 81 is arranged in one direction. As more color tiles 81 are arranged, the color tile member 80a becomes longer; thus, when the number of color tiles 81 to be used is larger, it becomes more difficult to manufacture the color tile member 80a planarly.

In view of the above, the second embodiment employs a plurality of color tile members 80b each containing fewer color tiles 81. FIG. 10 is a perspective view of the two color tile members 80b that can be attached to a colorimetric device 1b (FIG. 11) according to the second embodiment. When these are distinguished, the color tile members 80b are described as color tile members 80b1 and 80b2. Although the two color tile members 80b are used in the second embodiment, the number of color tile members 80b is not limited to two and may be any plural number.

Each of the color tile members 80b1 and 80b2 has a structure in which a plurality of color tiles 81 is arranged in one direction. Each of the color tile members 80b1 and 80b2 includes seven color tiles 81. The color tile member 80a illustrated in FIG. 5 includes 14 color tiles 81, and these color tiles 81 are divided into two groups; the color tile member 80b1 includes one group of color tiles 81 and the color tile member 80b2 includes the other group of color tiles 81.

Note that the tiles included in each of the color tile member 80b1 and 80b2 may be made different in accordance with the purpose of examining the accuracy of the colorimetric device 1b (FIG. 11) according to the second embodiment. For example, the color tile member 80b1 includes a white tile, a plurality of gray tiles with different gray densities, and a black tile, which are used to examine the intensity of the light received by the colorimetric unit 40. On the other hand, the color tile member 80b2 includes a plurality of tiles with different colors and high chroma, which are used to examine the wavelength of the light received by the colorimetric unit 40.

The color tile member 80b contains fewer color tiles 81 than the color tile member 80a illustrated in FIG. 5, so that the color tile member 80b is shorter than the color tile member 80a.

The structure of the color tile member 80b is the same as that of the color tile member 80a except the aforementioned point.

Figure 11:
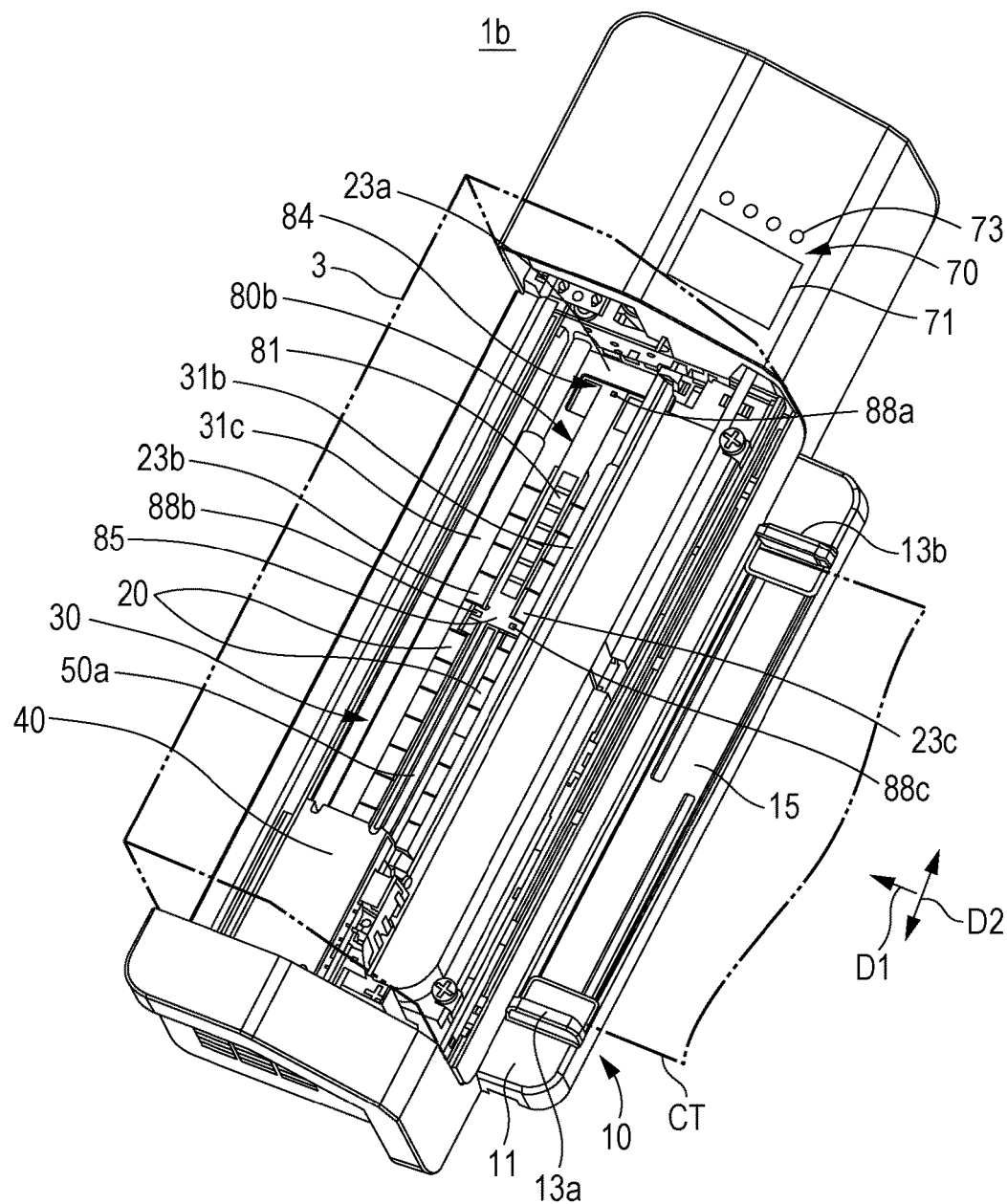
FIG. 11 is a perspective view of an external appearance of the colorimetric device according to the second embodiment to which the color tile member is attached.

FIG. 11 is a perspective view of an external appearance of the colorimetric device 1b according to the second embodiment to which the color tile member 80b is attached. FIG. 11 is different from FIG. 6 in that one of the two color tile members 80b is disposed on the backing member 50a instead of the color tile member 80a.

The user of the colorimetric device 1b first places one of the two color tile members 80b on the backing member 50a and then measures the color of the color tiles 81 included in the color tile member 80b with the use of the colorimetric device 1b by the step described with reference to FIG. 9. After the measurement, the user extracts the color tile member 80b from the colorimetric device 1b. Then, the user places the other of the two color tile members 80b on the backing member 50a and then measures the color of the color tiles 81 included in the color tile member 80b with the use of the colorimetric device 1b by the step described with reference to FIG. 9.

According to the second embodiment, the color tile member 80b is not just one but is divided in plural pieces. Therefore, the length of each of the color tile members 80b1 and 80b2 can be reduced, so that the increase in difficulty in manufacturing the color tile member 80b planarly can be suppressed.

A third embodiment will be described. In the second embodiment, it is necessary to exchange the color tile member 80b (FIG. 11) to be disposed on the backing member 50a. In the third embodiment, a plurality of color tile members 80c can be disposed altogether on the backing member 50a. This can omit the time and effort to exchange the color tile member 80c in the colorimetry.

Figure 12:
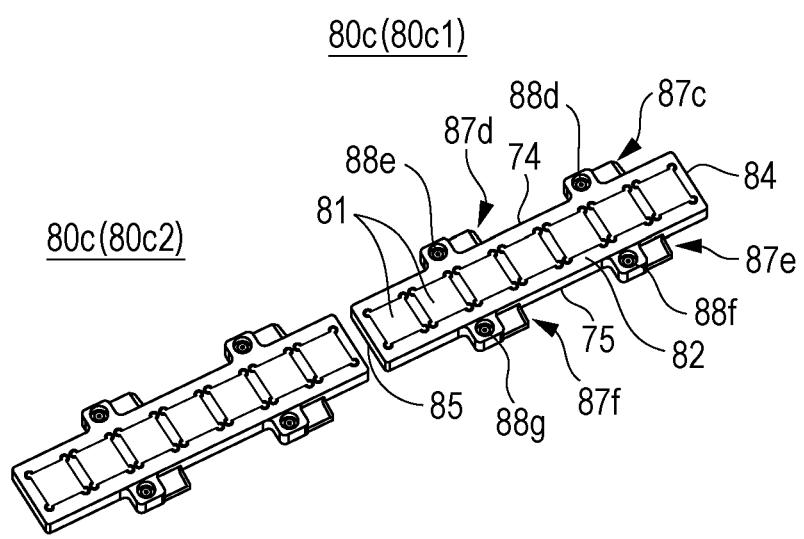
FIG. 12 is a perspective view of two color tile members that can be attached to a colorimetric device according to a third embodiment.

FIG. 12 is a perspective view of the two color tile members 80c that can be attached to a colorimetric device 1c (FIG. 13) according to the third embodiment. When these are distinguished, the color tile members are described as color tile members 80c1 and 80c2. Although the two color tile members 80c are used in the third embodiment, the number of color tile members 80c is not limited to two and may be any plural number.

The color tile member 80c is different from the color tile member 80b illustrated in FIG. 10 in the following point. The substrate 82 has two protrusions 87c and 87d protruding from one side part 74 of the substrate 82 in the longitudinal direction thereof, and two protrusions 87e and 87f protruding from the other side part 75. The protrusions 87c and 87e are positioned on the one end part 84 side of the substrate 82 and face each other. The protrusions 87d and 87f are positioned on the other end part 85 side of the substrate 82 and face each other.

The structure of the protrusions 87c, 87d, 87e, and 87f is the same as that of the protrusion 87a illustrated in FIG. 5 (the protrusion 87a and the protrusion 87b have the same structure). A ball plunger provided for the protrusion 87c is denoted by 88d, a ball plunger provided for the protrusion 87d is denoted by 88e, a ball plunger provided for the protrusion 87e is denoted by 88f, and a ball plunger provided for the protrusion 87f is denoted by 88g.

Figure 13:
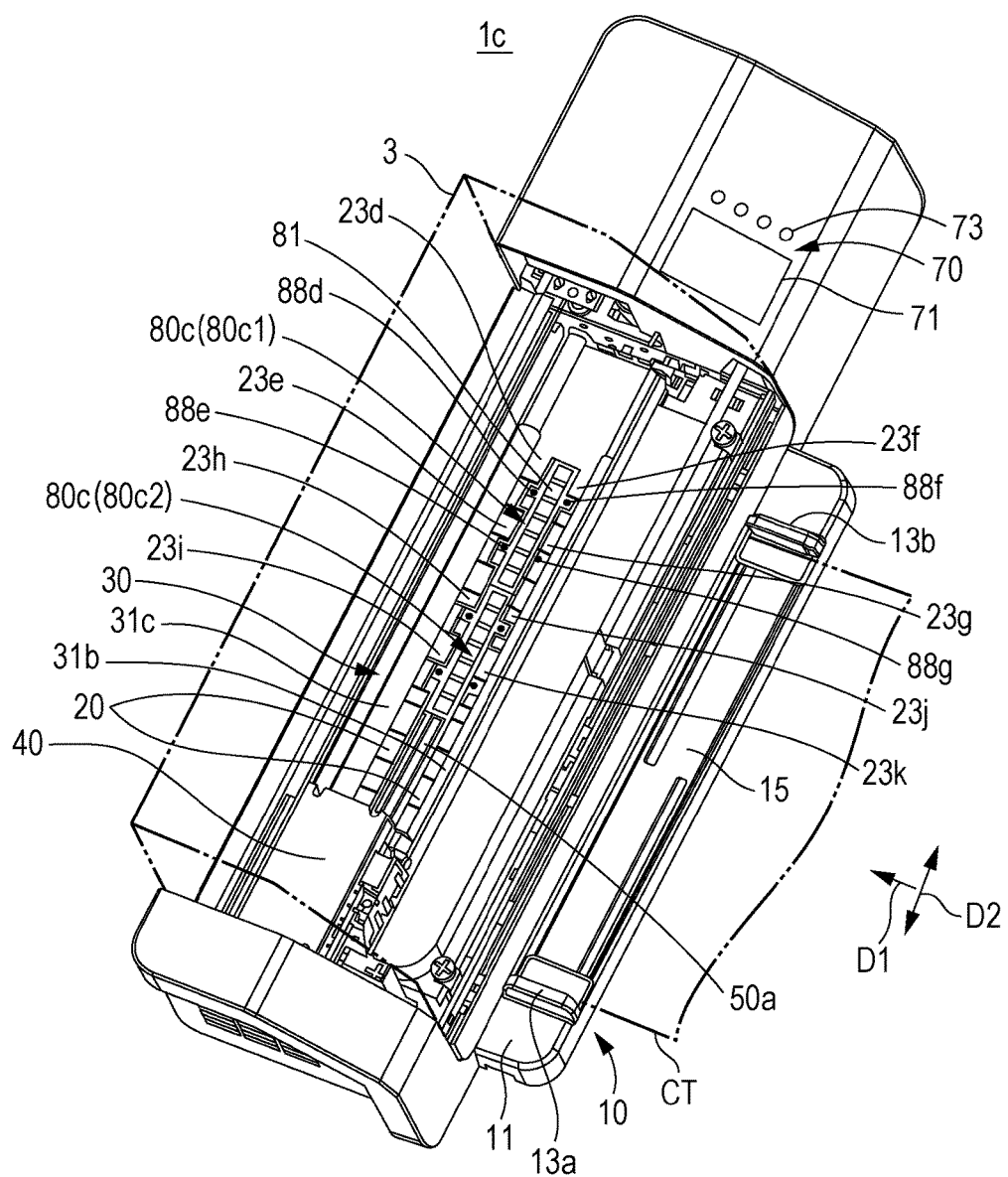
FIG. 13 is a perspective view of an external appearance of the colorimetric device according to the third embodiment to which the color tile member is attached.

FIG. 13 is a perspective view of an external appearance of the colorimetric device 1c according to the third embodiment to which the color tile member is attached. FIG. 13 is different from FIG. 11 in that the two color tile members 80c are arranged on the backing member 50a instead of the color tile member 80b in the longitudinal direction of the backing member 50a.

The color tile member 80c1 is held by holders 23d, 23e, 23f, and 23g corresponding to a part of the base member 20. The color tile member 80c2 is held by holders 23h, 23i, 23j, and 23k corresponding to a part of the base member 20.

The place where the color tile member 80c2 is disposed on the backing member 50a is the central part of the backing member 50a and is not the end side. Thus, the color tile member 80c2 is not held at three points but by four points. If the color tile member 80c1 and the color tile member 80c2 have the same structure, the manufacturing cost for the color tile members 80c1 and 80c2 can be reduced. Therefore, the color tile member 80c1 disposed on the side part of the backing member 50a is held at four points.

A modified example of the third embodiment will be described. While the two color tile members 80c held at four points are used in the third embodiment as illustrated in FIG.

12, a color tile member 80d1 held at three points and a color tile member 80d2 held at four points are used in the modified example.

Figure 14:
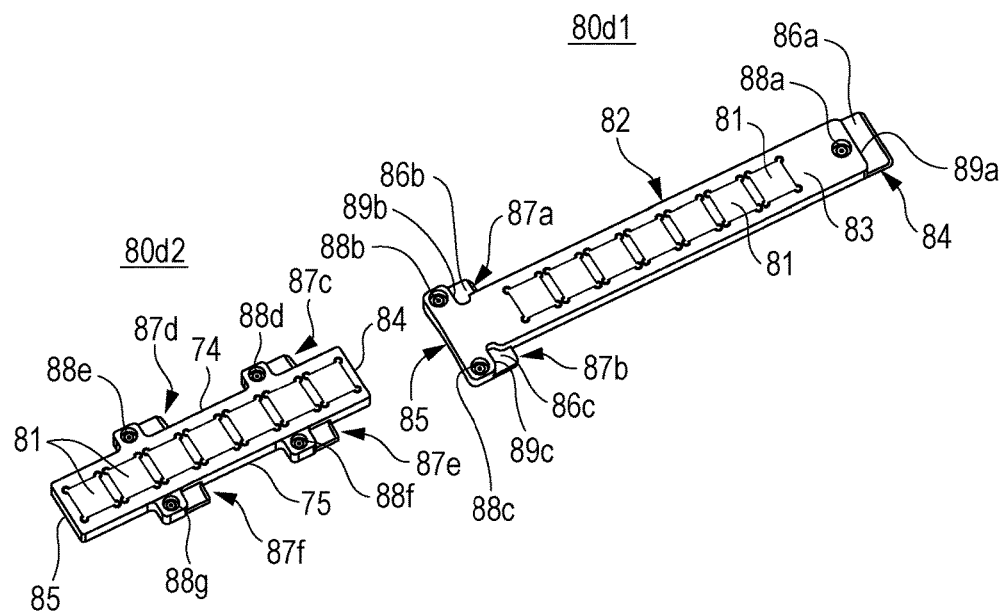
FIG. 14 is a perspective view of two color tile members that can be attached to a modified example of the colorimetric device according to the third embodiment.

FIG. 14 is a perspective view of the two color tile members 80d1 and 80d2 that can be attached to the modified example of the colorimetric device 1c according to the third embodiment. The color tile member 80d1 disposed on the side part of the backing member 50a is the type that is held at three points, which is similar to the color tile member 80b illustrated in FIG. 10. That is, the color tile member 80d1 is supported at three points by the holders 23a, 23b, and 23c as illustrated in FIG. 11. The color tile member 80d2 disposed in the central part of the backing member 50a is the type that is held at four points, which is similar to the color tile member 80c illustrated in FIG. 12. In other words, the color tile member 80d2 is held at four points by the holders 23h, 23i, 23j, and 23k as illustrated in FIG. 13.

According to the modified example of the third embodiment, the wrong placement of the color tile members 80d1 and 80d2 on the backing member 50a can be prevented. In the colorimetric devices 1a, 1b, and 1c according to the first to third embodiments, the control unit 4 (FIG. 4) stores in advance the order of color tiles 81 of which color is measured. Therefore, in the color tile member 80c illustrated in FIG. 12, the plurality of color tiles 81 is arranged in the order of measurement. Thus, if the place of the color tile member 80c1 and the place of the color tile member 80c2 are opposite, the color of the color tile 81 cannot be measured accurately.

In the modified example, the color tile member 80d1 is held at three points and the color tile member 80d2 is held at four points (i.e., the color tile member 80d1 and the color tile member 80d2 are held in the different shape). Therefore, the place of the color tile member 80d1 and the place of the color tile member 80d2 will not become opposite.

A fourth embodiment will be described. A colorimetric device according to the fourth embodiment corresponds to the colorimetric device 1a illustrated in FIG. 1 which includes a backing member 50b illustrated in FIG. 15 instead of the backing member 50a, and further includes a switching unit 100. Except this point, the colorimetric device according to the fourth embodiment has the same structure as the colorimetric device 1a.

Figure 15:
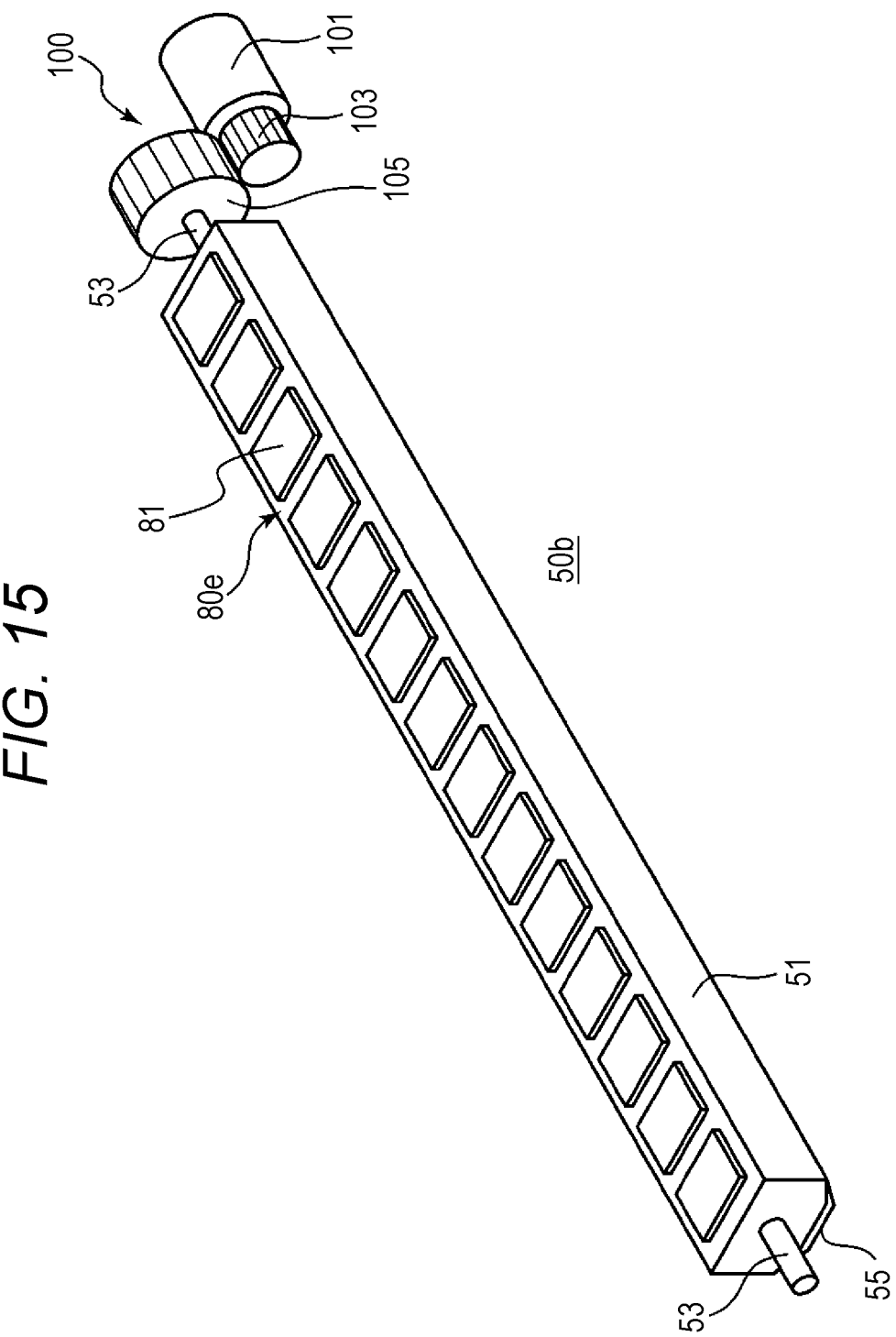
FIG. 15 is a perspective view of a backing member and a switching unit included in a colorimetric device according to a fourth embodiment.

FIG. 15 is a perspective view illustrating the backing member 50b and the switching unit 100 included in the colorimetric device according to the fourth embodiment. The backing member 50b includes a base member 51 with a first surface and a second surface, a background part 55 provided for the first surface, and a rotation shaft 53 provided for opposite ends of the base member 51.

The background part 55 becomes the background (background color) when the colorimetric unit 40 measures the color of the plurality of color patches CP included in the color chart CT illustrated in FIG. 3. The background part 55 is, for example, a white or black sheet.

The second surface of the backing member 50b is opposite to the first surface thereof where the background part 55 is provided, and the plurality of color tiles 81 is arranged in the longitudinal direction of the base member 51. The plurality of color tiles 81 constitutes a color tile member 80e.

The switching unit 100 includes, for example, a motor 101, a gear 103, and a gear 105. The gear 103 is fixed to the rotation shaft 53 of the motor 101, and is engaged with the gear 105. The gear 105 is fixed to one rotation shaft 53 of the base member 51. The rotation shaft 53 extends in the longitudinal direction of the base member 51.

As the motor 101 is rotated in accordance with the control of the control unit 4 (FIG. 4), the base member 51 can be rotated around the rotation shaft 53. This allows the backing member 50b to switch between a first posture illustrated in FIG. 16 and a second posture illustrated in FIG. 17.

With reference to FIG. 16, when the backing member 50b has the first posture, the background part 55 faces the colorimetric unit 40 at the colorimetric position P. With reference to FIG. 17, when the backing member 50b has the second posture, the color tile member 80e faces the colorimetric unit 40 at the colorimetric position P.

The sample surface S is a part of the surface of the color chart CT (FIG. 3) on which the color patch CP is printed, the part facing the colorimetric unit 40. The backing member 50b is attached to the base member 20 (FIG. 2) so that the height of the surface of the color tile 81 of the color tile member 80e coincides with the height of the sample surface S.

According to the fourth embodiment, the color tile member 80e is provided for the backing member 50b. Therefore, as compared to the case in which the color tile member 80e and the backing member 50b are provided separately, the attachment/detachment is unnecessary and the convenience is high and in addition, the space to install the color tile member 80e and the backing member 50b can be reduced. Thus, the size increase of the colorimetric device can be prevented and moreover, the color tile member 80e can be disposed quickly and easily and the measurement can be performed by the colorimetric device.

Figure 18:
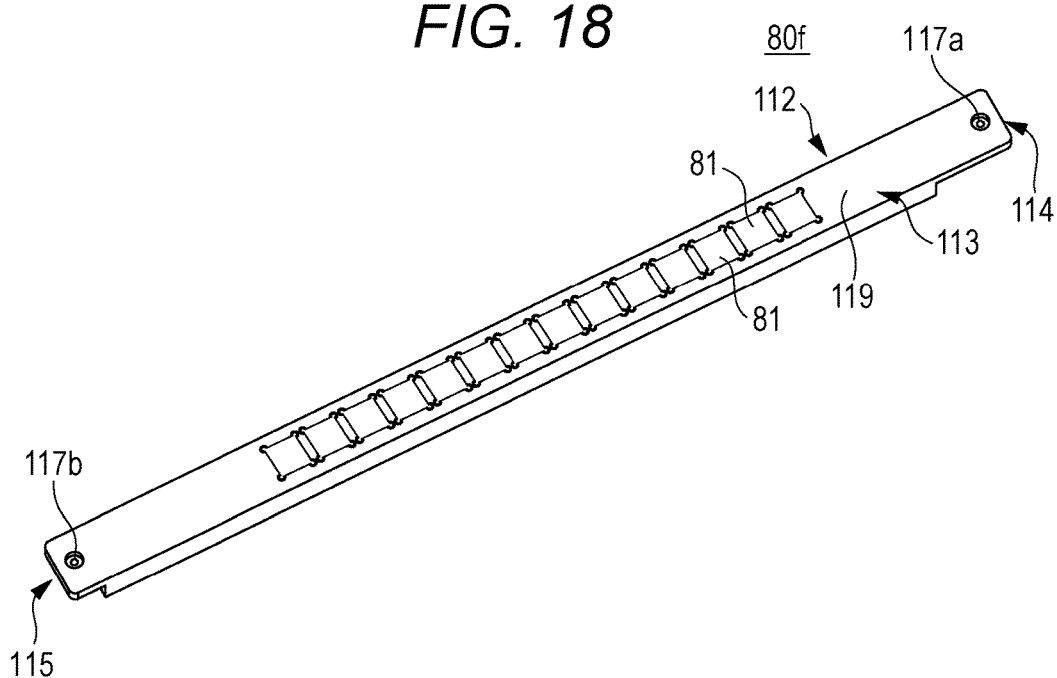
FIG. 18 is a perspective view of a color tile member that can be attached to a colorimetric device according to a fifth embodiment.
Figure 19:
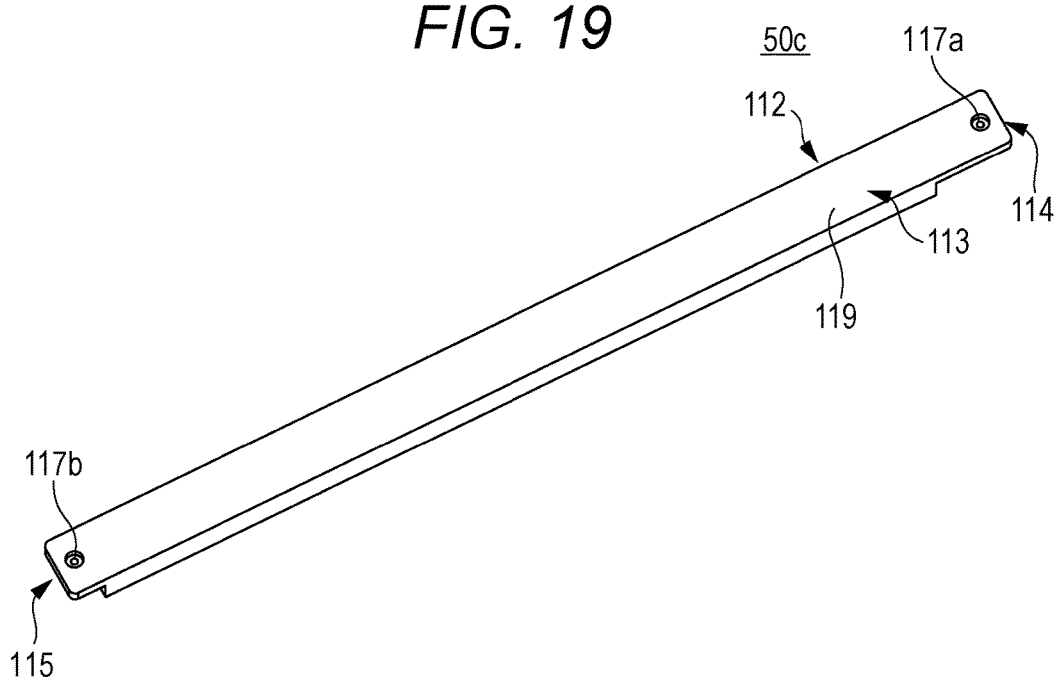
FIG. 19 is a perspective view of a backing member that can be attached to the colorimetric device according to the fifth embodiment.

A fifth embodiment will be described. FIG. 18 is a perspective view of a color tile member 80f that can be attached to a colorimetric device 1d (FIG. 20) according to the fifth embodiment. FIG. 19 is a perspective view of the backing member 50c that can be attached to the colorimetric device 1d according to the fifth embodiment. In the fifth embodiment, when the color of the color tile 81 is measured using the colorimetric device 1d, the backing member 50c is detached from the colorimetric device 1d and the color tile member 80f is attached to the colorimetric device 1d.

With reference to FIG. 18, the color tile member 80f includes the plurality of color tiles 81 and a substrate 112. The plurality of color tiles 81 is the same as the plurality of color tiles 81 included in the color tile member 80a illustrated in FIG. 5 and therefore the description thereto is omitted.

The substrate 112 has a long and narrow shape, and includes a main body part 113, and one end part 114 and the other end part 115 at opposite ends of the main body part 113. The plurality of color tiles 81 is arranged and fixed on a surface 119 of the main body part 113 in the longitudinal direction of the main body part 113.

On a back surface of the substrate 112, opposite ends of the main body part 113 have a step part. The thickness of the one end part 114 and the other end part 115 is smaller than the thickness of the main body part 113.

The one end part 114 and the other end part 115 function as the fixing device, and are respectively provided with a screw 117a and a screw 117b.

With reference to FIG. 19, the backing member 50c is the same as the color tile member 80f except that the plurality of color tiles 81 is not disposed, and the substrate 112 of the backing member 50c has the same shape and size as those of the substrate 112 of the color tile member 80f. The surface 119 of the main body part 113 of the backing member 50c becomes the background (background color) when the colorimetric unit 40 measures the color of the plurality of color patches CP included in the color chart CT illustrated in FIG. 3. The color of the surface 119 is, for example, white or black.

Figure 20:
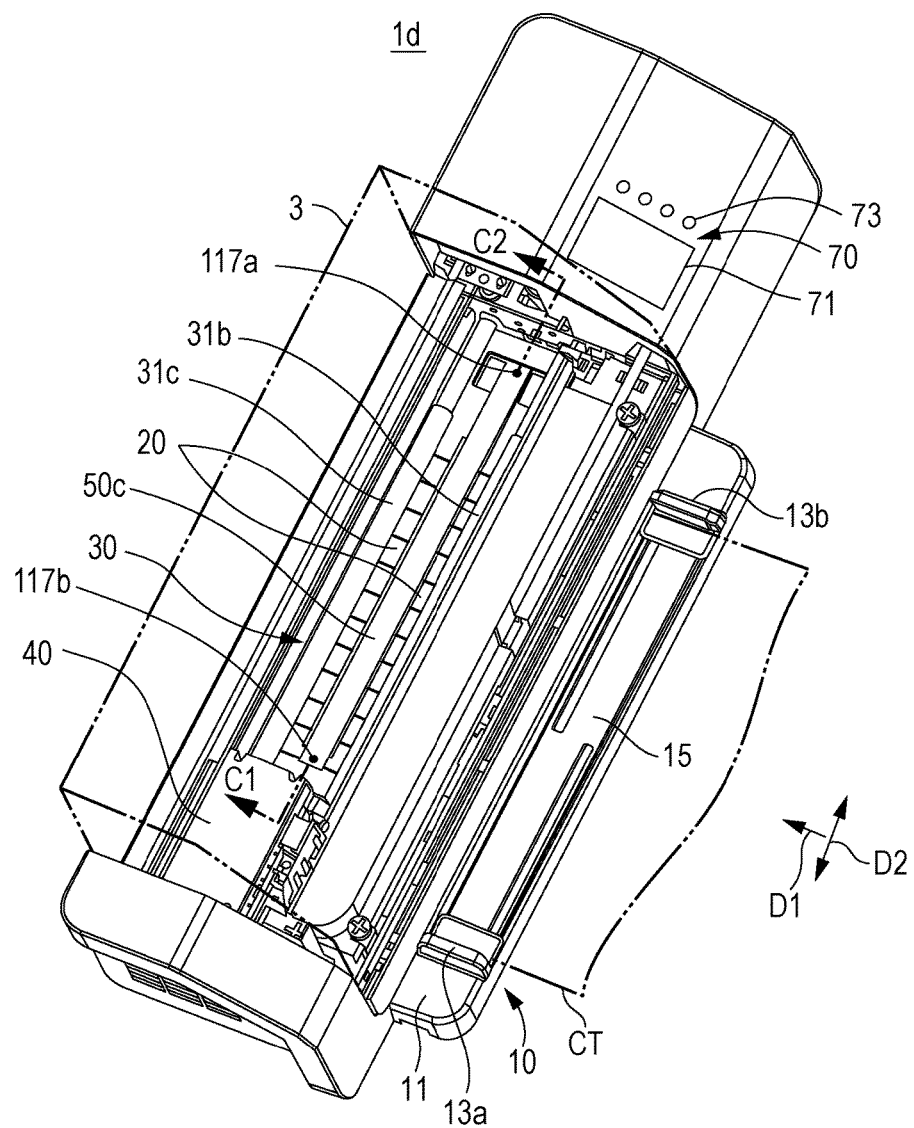
FIG. 20 is a perspective view of an external appearance of the colorimetric device according to the fifth embodiment to which the backing member is attached.
Figure 21:
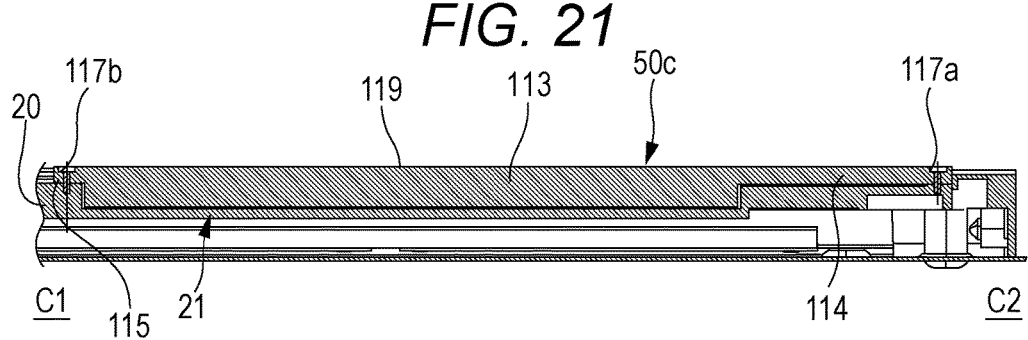
FIG. 21 is a cross-sectional view of the colorimetric device illustrated in FIG. 20, which is taken along a line C1-C2.

FIG. 20 is a perspective view of an external appearance of the colorimetric device 1d according to the fifth embodiment to which the backing member 50c is attached. FIG. 21 is a cross-sectional view of the colorimetric device 1d illustrated in FIG. 20, which is taken along a line C1-C2. The main body part 113 is fitted to the recessed part 21 of the base member 20 as illustrated in FIG. 2 with the surface 119 facing the colorimetric unit 40. With the screws 117a and 117b, the backing member 50c is fixed to the base member 20.

Figure 22:
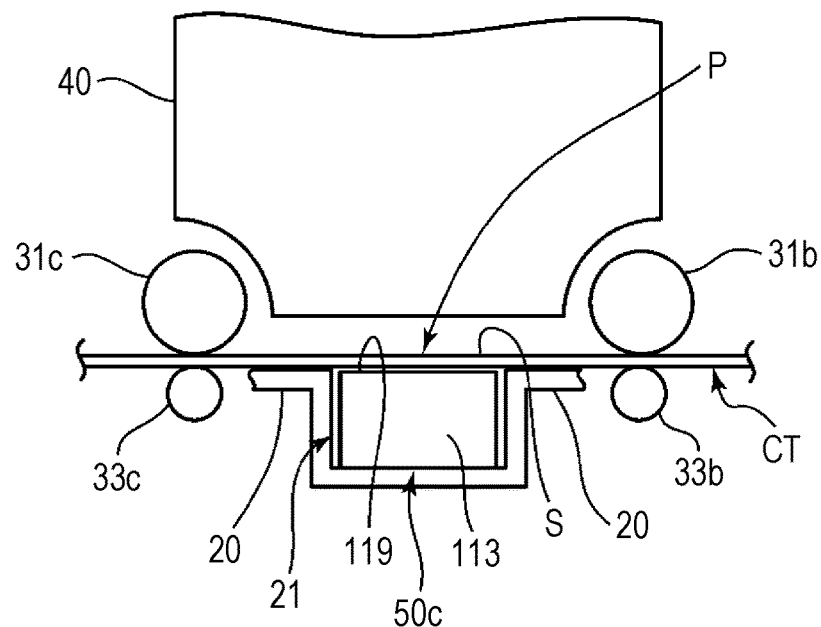
FIG. 22 is a schematic view illustrating a state in which the backing member is detachably attached to a recessed part of a base member in the fifth embodiment.
Figure 23:
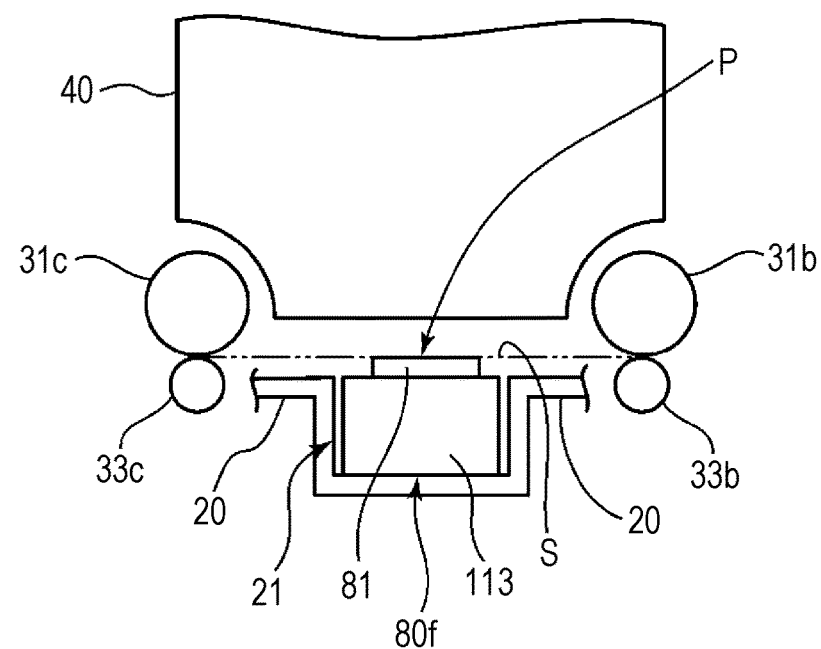
FIG. 23 is a schematic view illustrating a state in which the color tile member is detachably attached to the recessed part of the base member in the fifth embodiment.

FIG. 22 is a schematic view illustrating the state in which the backing member 50c is detachably attached to the recessed part 21 of the base member 20 in the fifth embodiment. FIG. 23 is a schematic view illustrating the state in which the color tile member 80f is detachably attached to the recessed part 21 of the base member 20 in the fifth embodiment. In the state that the backing member 50c is detached from the recessed part 21, the color tile member 80f is disposed in the recessed part 21 instead of the backing member 50c and fixed to the base member 20 with the screws 117a and 117b. The recessed part 21 functions as the attachment unit in which the backing member 50c or the color tile member 80f is detachably attached. The sample surface S is described in the fourth embodiment.

In the colorimetric device 1d according to the fifth embodiment, the backing member 50c is detached from the recessed part 21 (attachment unit) of the colorimetric device 1d and the color tile member 80f is attached to the recessed part 21 where the backing member 50c used to exist. Therefore, it is not necessary to provide the place exclusively used to dispose the color tile member 80f or to provide the colorimetric device 1d with the retraction space for the backing. This enables the color tile member 80f to be disposed in the colorimetric device 1d while preventing the size increase of the colorimetric device 1d.

Figure 24:
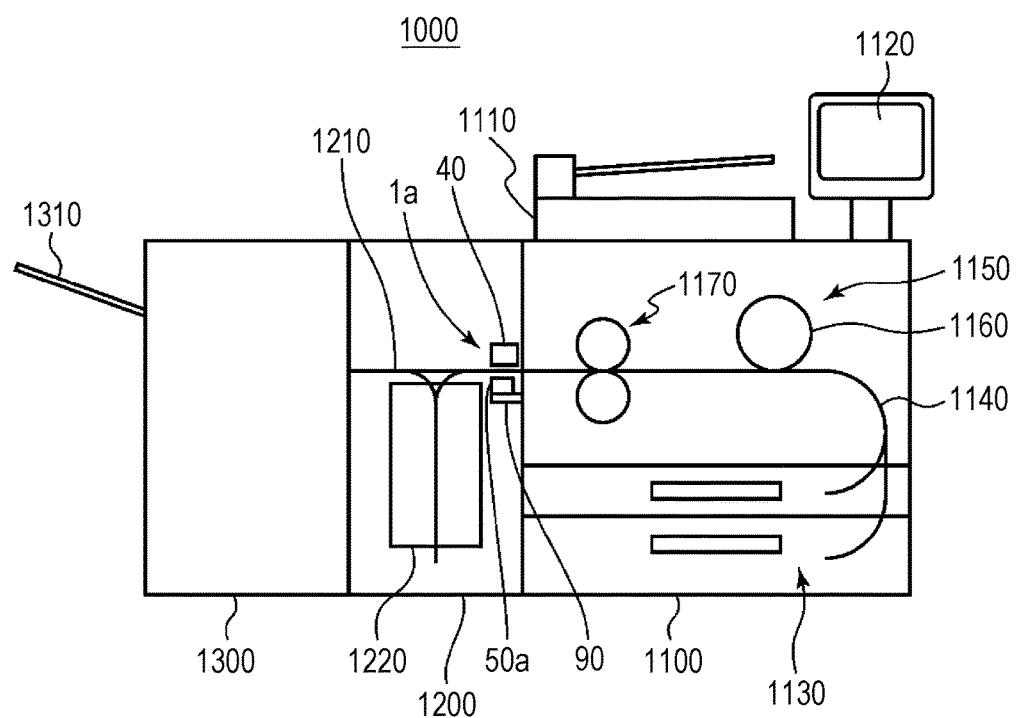
FIG. 24 is a schematic view illustrating a printing apparatus in which the colorimetric device according to the present embodiment is used.

Any of the colorimetric devices 1a, 1b, 1c, and 1d according to the present embodiments can be used for the printing apparatus. This will be described with reference to the example of the colorimetric device 1a illustrated in FIG. 1. FIG. 24 is a schematic view illustrating a printing apparatus 1000 in which the colorimetric device 1a is used. The colorimetric device 1a measures the color of the color patch formed on the sheet conveyed along a conveyance path 1210 in the calibration time.

The printing apparatus 1000 is a production printer, and has a printing speed of 100 or more sheets per minute. The printing apparatus 1000 includes a printing apparatus main body 1100, a relay device 1200, and a post-process device 1300.

The printing apparatus main body 1100 includes an automatic document feeder device 1110 disposed on the upper side thereof. The document fed by the automatic document feeder device 1110 is read by a scanner portion that is not shown. Note that the document can alternatively be read on a platen glass that is not shown.

The printing apparatus main body 1100 includes an operation display portion 1120 disposed on the upper side thereof. The operation display portion 1120 includes a touch panel, on which the manipulation by an operator and the information display are possible.

The printing apparatus main body 1100 includes a plurality of sheet feeding trays 1130 disposed on the lower side thereof.

The printing apparatus main body 1100 includes a conveyance unit 1140 that conveys the sheets fed by any of the sheet feeding trays 1130, and an image formation unit 1150 is provided in the middle of the conveyance unit 1140.

The image formation unit 1150 includes a photoreceptor 1160, and a charger, an LD, a developer, and a transferring unit, which are not shown, around the photoreceptor 1160. In the conveyance unit 1140 on the downstream side of the photoreceptor 1160, a fixer 1170 is disposed.

On the downstream side of the fixer 1170, the conveyance unit 1140 extends to be connected to a conveyance path 1210 of the relay device 1200.

The printing apparatus main body 1100 forms an image represented by the image data on the sheet conveyed along the conveyance unit 1140 by the electrophotography method. The sheet with the image formed thereon is conveyed to the fixer 1170.

The fixer 1170 heats the conveyed sheet so that the image is fixed on the sheet. The sheet after the fixing process is conveyed to the relay device 1200 by the conveyance unit 1140.

The relay device 1200 includes the conveyance path 1210 connected to the conveyance unit 1140 and moreover to the post-process device 1300 in the subsequent stage. The relay device 1200 includes an inversion/stack unit 1220 where a predetermined number of sheets conveyed along the conveyance path 1210 are inverted or stacked. The sheets stacked in the inversion/stack unit 1220 are conveyed to the post-process device 1300 side at a predetermined timing.

In the conveyance path 1210, the colorimetric device 1a is disposed on the upstream side of the inversion/stack unit 1220.

The colorimetric device 1a includes the colorimetric unit 40 disposed above the conveyance path 1210, the backing member 50a disposed below the conveyance path 1210 to face the colorimetric unit 40, and a supporter 90 that supports the backing member 50a.

The post-process device 1300 executes a predetermined post-process such as punching, folding, and saddle-stitching and stapling. The sheets conveyed from the relay device 1200 is subjected to the predetermined post-process in the post-process device 1300, and then discharged to a discharging unit 1310.

(Summary of embodiments) The colorimetric device according to the first aspect includes: a colorimetric unit that measures the color of a subject positioned at a predetermined colorimetric position; a conveyance unit that conveys a predetermined sheet to the colorimetric position; a backing member that is pressed by the predetermined sheet conveyed to the colorimetric position by the conveyance unit in a perpendicular direction relative to a surface of the predetermined sheet, and is disposed behind the predetermined sheet at the colorimetric position when viewed from the colorimetric unit; a supporter that supports the backing member in a manner that the backing member can move in the perpendicular direction; and a holder that holds the color tile member disposed on the backing member in a state that the amount of movement of the backing member in the perpendicular direction by a color tile member being thicker than the predetermined sheet and disposed on the backing member is larger than the amount of movement of the backing member in the perpendicular direction by the predetermined sheet.

The color of the backing member is, for example, white or black and the backing member becomes the background (background color) when the colorimetric unit measures the color of the predetermined sheet. The backing member is movable in the perpendicular direction relative to the surface of the predetermined sheet conveyed to the colorimetric position (i.e., the paper thickness direction). As the predetermined sheet becomes thicker, the amount of movement of the backing member is increased; as the predetermined sheet becomes less thick, the amount of movement of the backing member is decreased.

The colorimetric device according to the first aspect includes the holder that holds the color tile member disposed on the backing member. The color tile member is thicker than the predetermined sheet. The holder holds the color tile member in the state that the amount of movement of the backing member in the perpendicular direction by the color tile member disposed on the backing member is larger than the amount of movement of the backing member in the perpendicular direction by the predetermined sheet conveyed to the colorimetric position.

Therefore, even if the color tile member is thicker than the predetermined sheet, the colorimetric device according to the first aspect can measure the color of the color tile member disposed on the backing member. Thus, both the automatic measurement of the color chart and the measurement of the color tile member are possible while preventing the size increase of the colorimetric device.

In the above structure, the conveyance unit supports the predetermined sheet while the coordinate of the predetermined sheet in the perpendicular direction at the colorimetric position is set to a predetermined value, and the holder holds the color tile member while the coordinate of the surface of the color tile of the color tile member is set to the predetermined value.

In this structure, the coordinate in the perpendicular direction at the colorimetric position is the same on the predetermined sheet and on the surface of the color tile of the color tile member. Therefore, the distance from the optical system of the colorimetric unit to the predetermined sheet becomes the same as the distance from the optical system of the colorimetric unit to the surface of the color tile. As compared to the case in which these are different, the accuracy of examining the colorimetric device can be increased.

The above structure further includes the movement unit that moves the colorimetric unit in a direction orthogonal to the direction where the predetermined sheet is conveyed in the state that the colorimetric unit faces the backing member.

In this structure, the present invention is applied to the colorimetric device that performs the colorimetry on the predetermined sheet by moving the colorimetric unit in the main scanning direction and moving the predetermined sheet in the sub-scanning direction.

In the above structure, the color tile member has a structure in which a plurality of color tiles is arranged in one direction, and the holder holds one or a plurality of color tile members arranged on the backing member along the longitudinal direction of the backing member.

With this structure, an embodiment in which one color tile member is disposed on the backing member and an embodiment in which a plurality of color tile members is arranged on the backing member are given. In the latter embodiment, the following operation effect is achieved. When the plurality of divided color tile members is used instead of one color tile member, the length of each of the plurality of color tile members can be reduced, so that the increase in difficulty to manufacture each color tile member planarly can be suppressed. However, in the embodiment of the colorimetric device in which the colorimetry is performed by disposing one color tile member on the backing member, and then another colorimetry is performed by disposing the next color tile member on the backing member, it takes some time and effort to exchange the color tile members.

In the latter embodiment, the plurality of color tile members can be disposed altogether on the backing member; therefore, it is unnecessary to exchange the color tile member in the colorimetry.

In the above structure, the color tile member has a structure in which: the plurality of color tiles is arranged in one direction; two or more of the color tile members are disposed on the backing member in the longitudinal direction of the backing member; and the holder holds one color tile member and the other color tile member in the different holding shapes.

With this structure, one color tile member and the other color tile member are held in the different holding shapes, so that the wrong placement of the two color tile members on the backing member can be prevented.

The colorimetric device according to the second aspect includes: a colorimetric unit that measures the color of a subject positioned at a predetermined colorimetric position; a conveyance unit that conveys a predetermined sheet to the colorimetric position; a backing member that includes a base member with a first surface and a second surface, and a background part provided for the first surface and that is disposed behind the predetermined sheet which is conveyed by the conveyance unit to the colorimetric position, when viewed from the colorimetric unit; a color tile member provided for the second surface; and a switching unit that switches between a first posture that the background part faces the colorimetric unit and a second posture that the color tile member faces the colorimetric unit by rotating the base member at the colorimetric position.

The background part becomes the background (background color) when the colorimetric unit measures the color of the predetermined sheet. The switching unit can switch the first posture that the background part faces the colorimetric unit and the second posture that the color tile member faces the colorimetric unit. In this manner, in the colorimetric device according to the second aspect in which the color tile member is provided for the backing member, the space for installing the color tile member and the backing member can be reduced as compared to the case in which the color tile member and the backing member are provided separately. Therefore, the color tile member can be disposed in the colorimetric device while the size increase of the colorimetric device is prevented.

The colorimetric device according to the third aspect includes: a colorimetric unit that measures the color of a subject positioned at a predetermined colorimetric position; a conveyance unit that conveys a predetermined sheet to the colorimetric position; an attachment unit to which a backing member disposed behind the predetermined sheet conveyed to the colorimetric position by the conveyance unit when viewed from the colorimetric unit is detachably attached; and a color tile member that is detachably attached to the attachment unit instead of the backing member in a state that the backing member is detached.

In the colorimetric device according to the third aspect, the backing member is detached from the attachment unit provided for the colorimetric device and the color tile member is attached to this attachment unit. This eliminates the necessity to provide the colorimetric device with a place exclusively used to dispose the color tile member. Therefore, the color tile member can be disposed in the colorimetric device while the size increase of the colorimetric device is prevented.

The entire disclosure of Japanese Patent Application No. 2014-253937 filed on Dec. 16, 2014 including description, claims, drawings, and abstract are incorporated herein by reference in its entirety.

To express the present invention, the present invention has been described appropriately and sufficiently through the embodiments as above with reference to the drawings, but it is to be understood that those who are skilled in the art can easily modify/improve the above embodiments. Thus, such modifications or improvements made by those who are skilled in the art are construed as being included in the scope of claims, unless those modifications and improvements depart from the scope of rights according to the scope of claims.

The invention claimed is:

1. A colorimetric device comprising:
a colorimetric unit that measures a color of a subject positioned at a predetermined colorimetric position;
a conveyance unit that conveys a predetermined sheet to the colorimetric position;
a backing member that is pressed by the predetermined sheet conveyed to the colorimetric position by the conveyance unit in a perpendicular direction relative to a surface of the predetermined sheet, and is disposed behind the predetermined sheet at the colorimetric position when viewed from the colorimetric unit;
a supporter that supports the backing member in a manner that the backing member can move in the perpendicular direction; and
a holder that holds the color tile member disposed on the backing member in a state that the amount of movement of the backing member in the perpendicular direction by a color tile member being thicker than the predetermined sheet and disposed on the backing member is larger than the amount of movement of the backing member in the perpendicular direction by the predetermined sheet.

2. The colorimetric device according to claim 1, wherein the conveyance unit supports the predetermined sheet while setting a coordinate of the predetermined sheet in the perpendicular direction at the colorimetric position to a predetermined value, and
the holder holds the color tile member while setting the coordinate of a surface of a color tile of the color tile member to the predetermined value.

3. The colorimetric device according to claim 1, further comprising a movement unit that moves the colorimetric unit in a direction orthogonal to the direction where the predetermined sheet is conveyed in a state that the colorimetric unit faces the backing member.

4. The colorimetric device according to claim 1, wherein the color tile member has a structure in which a plurality of color tiles is arranged in one direction, and
the holder holds one or a plurality of color tile members arranged on the backing member along a longitudinal direction of the backing member.

5. The colorimetric device according to claim 1, wherein the color tile member has a structure in which a plurality of color tiles is arranged in one direction,
two or more of the color tile members are arranged on the backing member along the longitudinal direction of the backing member, and
the holder holds one color tile member and the other color tile member in different holding shapes.

6. A colorimetric device comprising:
a colorimetric unit that measures a color of a subject positioned at a predetermined colorimetric position;
a conveyance unit that conveys a predetermined sheet to the colorimetric position;
an attachment unit to which a backing member disposed behind the predetermined sheet conveyed to the colorimetric position by the conveyance unit when viewed from the colorimetric unit is detachably attached; and
a color tile member that is detachably attached to the attachment unit instead of the backing member in a state that the backing member is detached, wherein the color tile member is attached so that the height of the surface of the color tile coincides with the height of the sheet.

7. A printing apparatus comprising:
a conveyance unit that conveys a sheet;
an image formation unit that forms an image represented by image data on the sheet conveyed using the conveyance unit; and
the colorimetric device according to claim 1 for measuring a color of the image formed on the sheet.

8. The colorimetric device according to claim 2, further comprising a movement unit that moves the colorimetric unit in a direction orthogonal to the direction where the predetermined sheet is conveyed in a state that the colorimetric unit faces the backing member.

9. The colorimetric device according to claim 2, wherein the color tile member has a structure in which a plurality of color tiles is arranged in one direction, and
the holder holds one or a plurality of color tile members arranged on the backing member along a longitudinal direction of the backing member.

10. The colorimetric device according to claim 2, wherein the color tile member has a structure in which a plurality of color tiles is arranged in one direction,
two or more of the color tile members are arranged on the backing member along the longitudinal direction of the backing member, and
the holder holds one color tile member and the other color tile member in different holding shapes.

11. A printing apparatus comprising:
a conveyance unit that conveys a sheet;
an image formation unit that forms an image represented by image data on the sheet conveyed using the conveyance unit; and
the colorimetric device according to claim 2 for measuring a color of the image formed on the sheet.

12. The colorimetric device according to claim 3, wherein the color tile member has a structure in which a plurality of color tiles is arranged in one direction, and
the holder holds one or a plurality of color tile members arranged on the backing member along a longitudinal direction of the backing member.

13. The colorimetric device according to claim 3, wherein the color tile member has a structure in which a plurality of color tiles is arranged in one direction,
two or more of the color tile members are arranged on the backing member along the longitudinal direction of the backing member, and
the holder holds one color tile member and the other color tile member in different holding shapes.

14. A printing apparatus comprising:
a conveyance unit that conveys a sheet;
an image formation unit that forms an image represented by image data on the sheet conveyed using the conveyance unit; and
the colorimetric device according to claim 3 for measuring a color of the image formed on the sheet.

15. A printing apparatus comprising:
a conveyance unit that conveys a sheet;
an image formation unit that forms an image represented by image data on the sheet conveyed using the conveyance unit; and
the colorimetric device according to claim 4 for measuring a color of the image formed on the sheet.

16. A printing apparatus comprising:
a conveyance unit that conveys a sheet;
an image formation unit that forms an image represented by image data on the sheet conveyed using the conveyance unit; and
the colorimetric device according to claim 5 for measuring a color of the image formed on the sheet.

17. A printing apparatus comprising:
a conveyance unit that conveys a sheet;
an image formation unit that forms an image represented by image data on the sheet conveyed using the conveyance unit; and
the colorimetric device according to claim 6 for measuring a color of the image formed on the sheet.

\* \* \* \* \*